US009012171B2

(12) United States Patent
Smilansky

(10) Patent No.: US 9,012,171 B2
(45) Date of Patent: Apr. 21, 2015

(54) SYSTEMS AND METHODS FOR MEASURING TRANSLATION ACTIVITY IN VIABLE CELLS

(75) Inventor: Ze'ev Smilansky, M.P. Emek Soreq (IL)

(73) Assignee: Anima Cell Metrology, Inc., Bernardsville, NJ (US)

( * ) Notice: Subject to any disclaimer, the term of this patent is extended or adjusted under 35 U.S.C. 154(b) by 564 days.

(21) Appl. No.: 12/682,212

(22) PCT Filed: Oct. 7, 2008

(86) PCT No.: PCT/IL2008/001328
§ 371 (c)(1),
(2), (4) Date: Jun. 17, 2010

(87) PCT Pub. No.: WO2009/047760
PCT Pub. Date: Apr. 16, 2009

(65) Prior Publication Data
US 2010/0267030 A1    Oct. 21, 2010

Related U.S. Application Data

(60) Provisional application No. 60/978,420, filed on Oct. 9, 2007, provisional application No. 61/086,165, filed on Aug. 5, 2008.

(51) Int. Cl.
C12Q 1/02      (2006.01)
G01N 33/52    (2006.01)
G01N 33/50    (2006.01)
G01N 33/68    (2006.01)

(52) U.S. Cl.
CPC ............ *G01N 33/5005* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 5,626,058 A | 5/1997 | Karpowich et al. | |
| 5,643,722 A | 7/1997 | Rothschild et al. | |
| 5,706,498 A | 1/1998 | Fujimiya et al. | |
| 5,777,079 A | 7/1998 | Tsien et al. | |
| 5,856,928 A | 1/1999 | Yan | |
| 5,922,858 A | 7/1999 | Rothschild et al. | |
| 6,189,013 B1 | 2/2001 | Maslyn et al. | |
| 6,210,941 B1 | 4/2001 | Rothchild | |
| 7,015,486 B1 | 3/2006 | Sarbach | |
| 7,288,372 B2 | 10/2007 | Olejnik | |
| 7,388,125 B2 | 6/2008 | Ristic et al. | |
| 7,807,349 B2 | 10/2010 | Smilansky | |
| 2003/0092031 A1 | 5/2003 | Rothchild | |
| 2003/0219780 A1 | 11/2003 | Olejnik | |
| 2003/0219783 A1 | 11/2003 | Puglisi | |
| 2004/0023256 A1 | 2/2004 | Puglisi | |
| 2004/0023874 A1 | 2/2004 | Burgess et al. | |
| 2004/0235175 A1 | 11/2004 | Gaudernack | |
| 2005/0118151 A1 | 6/2005 | Larsen | |
| 2005/0157294 A1 | 7/2005 | Hopkins | |
| 2005/0164264 A1 | 7/2005 | Shipwash | |
| 2006/0228708 A1 | 10/2006 | Smilansky | |
| 2007/0021597 A1 | 1/2007 | Edwards | |
| 2007/0134814 A1 | 6/2007 | Kajander | |
| 2009/0081643 A1 | 3/2009 | Preminger et al. | |
| 2011/0262899 A1 | 10/2011 | Cooperman et al. | |
| 2012/0183957 A1 | 7/2012 | Smilansky et al. | |

FOREIGN PATENT DOCUMENTS

| | | |
|---|---|---|
| DE | 4410655 A1 | 9/1995 |
| EP | 1428016 | 4/2008 |
| WO | 94/02595 | 2/1994 |
| WO | 0116375 A2 | 3/2001 |
| WO | 0118243 A1 | 3/2001 |
| WO | 03/052067 | 6/2003 |
| WO | 03/057164 | 7/2003 |
| WO | 03064604 A2 | 8/2003 |
| WO | WO 2004050825 A2 * | 6/2004 |
| WO | 2005/001062 | 1/2005 |
| WO | 2005/116252 | 12/2005 |
| WO | 2007/002758 | 1/2007 |
| WO | 2008/028298 | 3/2008 |
| WO | 2009047760 A2 | 4/2009 |

OTHER PUBLICATIONS

Brady et al. Hepatic carnitine palmitoyltransferase turnover and translation rates in fed, starved, streptozotocin-diabetic and diethylhexyl phthalate-treated rats. Biochemical Journal, vol. 246, pp. 641-649, 1987.*
Bevan et al. Identifying small-molecule lead compounds: the screening approach to drug discovery. Trends in Biotechnology, vol. 13, No. 3, pp. 115-121, Mar. 1995.*
Vukojevic et al. Study of molecular events in cells by fluorescence correlation spectroscopy. CMLS, Cellular and Molecular Life Sciences, vol. 62, pp. 535-550, 2005.*
Magde et al. Fluorescence Correlation Spectroscopy. II. An Experimental Realization. Biopolymers, vol. 13, pp. 29-61, 1974.*
Agrawal et al, (2007) "Visualization of tRNA Movements on the *Escherichia coli* 70s Ribosome During the Elongation Cycle," The Journal of Cell Biology, 150(3):447-459.
Akhtar et al., (1992) "Cellular uptake and intracellular fate of antisense oligonucleotides," Trends Cell Biology, 2(5):139-144.
Barhoom et al., (2011) "Quantitative single cell monitoring of protein synthesis at subcellular resolution using fluorescently labeled tRNA," Nucleic Acids Research, 39(19):e129.
Barhoom et al., (2013) "Dicodon monitoring of protein synthesis (DiCoMPS) reveals levels of synthesis of a viral protein in single cells," Nucleic Acids Research, 41(18):e177.

(Continued)

*Primary Examiner* — Jennifer Dunston
(74) *Attorney, Agent, or Firm* — Winston & Strawn LLP

(57) ABSTRACT

Systems for measuring protein translation and methods for measuring overall translation activity in viable cells or subcellular compartments is disclosed. The methods identify general ribosomal activity, if desired at sub-cellular resolution, thereby providing a signal indicating the rate of any of the steps of protein synthesis selected from initiation, elongation, termination or recycling. The translation system can be used to identify translation modulators in high-throughput-screening (HTS).

15 Claims, 4 Drawing Sheets

(56) References Cited

OTHER PUBLICATIONS

Figure 1:
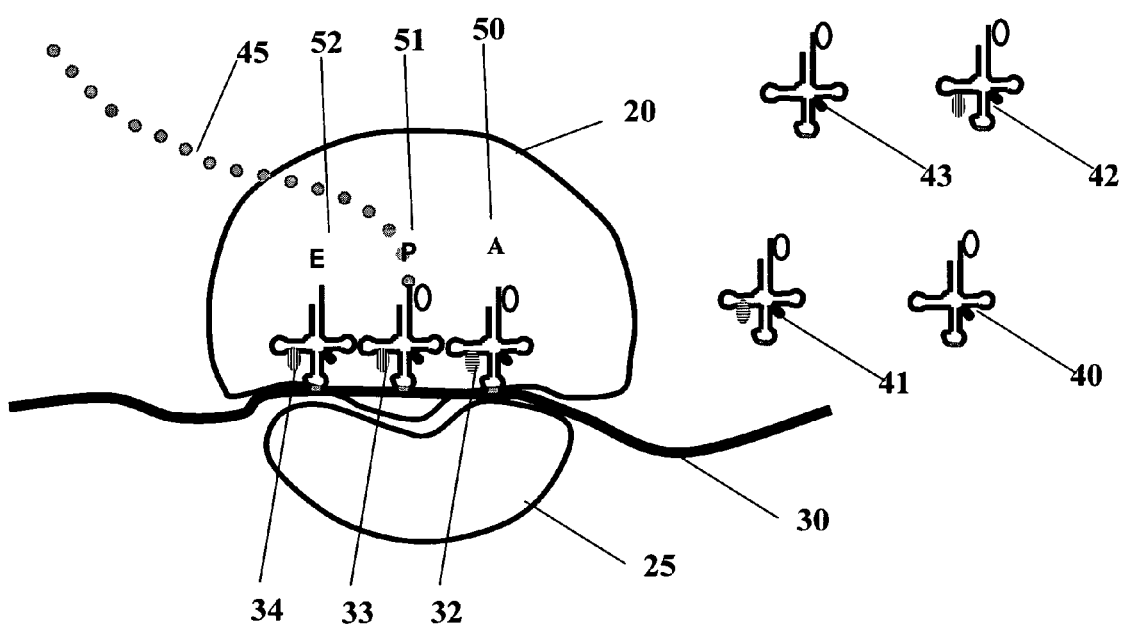

Blanchard et al., (2004) "tRNA selection and kinetic proofreading in translation," Nature Structural & Molecular Biology, 11(10)1008-1014.
Cohen, (1992) "Epidemiology of Drug Resistance: Implications for a Post-Antimicrobial Era," Science, 257(5073):1050-1055.
Dittmar et al., (2005) "Selective charging of tRNA isoacceptors induced by amino-acid starvation," EMBO Reports, 6(2):151-157.
Gräf et al., (2005) "Live Cell Spinning Disk Microscopy," Adv Biochem Engin/Biotechnol, 95:57-75.
Gygi et al., (1999) "Quantitative analysis of complex protein mixtures using isotope-coded affinity tags," Nature Biotechnology, 17:994-999.
Ha, (2001) "Single-Molecule FRET," Single Mol., 2(4):283-284.
Hailey et al., (2002) "Fluorescence Resonance Energy Transfer Using Color Variants of Green Fluorescent Protein," Methods in Enzymology, 351:34-49.
Helmchen et al., (2005) "Deep tissue two-photon microscopy," Nature Methods, 2(12):932-940.
Huang et al., (1975) "Studies of 30 S *Escherichia coli* Ribosome Reassembly Using Individual Proteins Labeled with an Environmentally Sensitive Fluorescent Probe," J. Mol. Biol., 97(4):423-441.
Humphery-Smith et al., (1997) "Proteome research: Complementarity and limitations with respect to the RNA and DNA worlds," Electrophoresis, 18(8):1217-1242.
Jenkins et al., (2001) "Arrays for protein expression profiling: Towards a viable alternative to two-dimensional gel electrophoresis?" Proteomics, 1(1):13-29.
Johnson, (2005) "The co-translational folding and interactions of nascent protein chains: a new approach using fluorescence resonance energy transfer," FEBS Letters, 579(4):916-920.
Kapp et al., (2004) "The Molecular Mechanics of Eukaryotic Translation," Annu. Rev. Biochem., 73:657-704.
Langlois et al., (1975) "A Comparison of the Fluorescence of the Y Base of Yeast tRNA-Phe in Solution and in Crystals," Biochemistry, 14(11):2554-2258.
Marshall et al., (2008) "Irreversible chemical steps control intersubunit dynamics during translation," Proc. Natl. Acad. Sci. USA, 105(40):15364-15369 and supporting information (9 pages).
Negrutskii et al., (1991) "Channeling of aminoacyl-tRNA for protein synthesis in vivo," Proc. Natl. Acad. Sci. USA, 88(11):4991-4995.
Negrutskii et al., (1994) "Supramolecular organization of the mammalian translation system," Proc. Natl. Acad. Sci. USA, 91(3):964-968.
Nolkrantz et al., (2001) "Electroporation of Single Cells and Tissues with an Electrolyte-filled Capillary," Anal. Chem., 73(18):4469-4477.
Nyborg et al., (1998) "Protein biosynthesis: structural studies of the elongation cycle," FEBS Letters, 430(1-2):95-99.
Olofsson et al., (2003) "Single-cell electroporation," Current Opinion in Biotechnology, 14(1):29-34.
Ramakrishnan, (2002) "Ribosome Structure and the Mechanism of Translation," Cell, 108(4):557-572.
Rathenberg et al., (2003) "High-efficiency transfection of individual neurons using modified electrophysiology techniques," Journal of Neuroscience Methods, 126(1):91-98.
Rodnina et al., (2005) "Recognition and selection of tRNA in translation," FEBS Letters, 579(4):938-942.
Ryttsén et al., (2000) "Characterization of Single-Cell Electroporation by Using Patch-Clamp and Fluorescence microscopy," Biophysical Journal, 79(4):1993-2001.
Schlünzen et al., (2001) "Structural basis for the interaction of antibiotics with the peptidyl transferase centre in eubacteria," Nature, 413(6858):814-821.
Vestweber et al., (1989) "DNA-protein conjugates can enter mitochondria via the protein import pathway," Nature, 338(6211):170-172.
Watson et al., (1995) "Macromolecular Arrangement in the Aminoacyl-tRNA•Elongation Factor Tu•GTP Ternary Complex. A Fluorescence Energy Transfer Study," Biochemistry, 34(24):7904-7912.
Wintermeyer et al., (1971) "Replacement of Y base, dihydrouracil, and 7-methylguanine in tRNA by artificial odd bases," FEBS Letters, 18(2):214-218.
Yokoo et al., (2008) "Generation of a Transplantable Erythropoietin-Producer Derived From Human Mesenchymal Stem Cells," Transplantation, 85(11):1654-1658.
Agmon et al., "On peptide bond formation, translocation, nascent protein progression and the regulatory properties of ribosomes", Eur. J. Biochem., vol. 270, pp. 2543-2556 (2003).
Akerman et al., "Nanocrystal targeting in vivo", Proc. Natl. Acad. Sci. USA, vol. 99, No. 20, pp. 12617-12621 (2002).
Bain et al., "Site-specific incorporation of non-natural residues during in vitro protein biosynthesis with semisynthetic aminoacyl-tRNAs", Biochemistry, vol. 30, pp. 5411-5421 (1991).
Bastiaens et al., "Fluorescence lifetime imaging microscopy: spatial resolution of biochemical processes in the cell", Trends in Cell Biol., vol. 9, pp. 48-52 (1999).
Baubet et al., "Chimeric green fluorescent protein-aequorin as bioluminescent Ca2+ reporters at the single-cell level", Proc. Natl. Acad. Sci. USA, vol. 97, No. 13, pp. 7260-7265 (2000).
Braslavsky et al., "Sequence information can be obtained from single DNA molecules", Proc. Natl. Acad. Sci. USA, vol. 100, No. 7, pp. 3960-3964 (2003).
Campagnola et al. "Second-harmonic imaging microscopy for visualizing biomolecular arrays in cells, tissues and organisms", Nat. Biotechnol., vol. 21, No. 11, ppl. 1356-1360 (2003).
Chang et al., "Significance of molecular signaling for protein translation control in neurodegenerative diseases", Neurosignals. vol. 15, pp. 249-258 (2006).
Cload et al., "Development of improved tRNAs for in vitro biosynthesis of proteins containing unnatural amino acids", Chem. Biol. 3, pp. 1033-1038 (1996).
Cooperman, "Affinity labeling of ribosomes", Methods Enzymol., vol. 164, pp. 341-361 (1988).
Cooperman, et al., "Photolabile derivatives of oligonucleotides as probes of ribosomal struture" Methods Enzymol., vol. 318, pp. 118-136 (2000).
Cornish et al., "Site-specific incorporation of biophysical probes into proteins", Proc. Natl. Acad. Sci. USA, vol. 91, pp. 2910-2914 (1994).
De Angelis, "Why FRET over genomics?", Physiol. Genomics, vol. 1, No. 2, pp. 93-99 (1999).
Deniz et al., "Single-molecule protein folding: diffusion fluorescence resonance energy transfer studies of the denaturation of chymotrypsin inhibitor 2", Proc. Natl. Acad. Sci. USA, vol. 97, No. 10, pp. 5179-5184 (2000).
Denk et al., "Two-photon laser scanning fluorescence microscopy", Science, vol. 248, pp. 73-76 (1990).
Dubertret et al., "In vivo imaging of quantum dots encapsulated in phospholipid micelles", Science, vol. 298, pp. 1759-1762 (2002).
Emptage "Fluorescent imaging in living systems", Curr. Opin. Pharmacol., vol. 1, No. 5, pp. 521-525 (2001).
Erdogan et al., "Detection of mitochondrial single nucleotide polymorphisms using a primer elongation reaction on oligonucleotide microarrays", Nucleic Acids Res., vol. 29, No. 7, E36 (2001).
Fuchs et al., "Flow cytomeric anaylsis of the in situ accessibility of *Escherichia coli* 16S rRNA for fluorescently labeled oligonucleotide probes", Appl. Environ. Microbiol., vol. 64, No. 12, pp. 4973-4982 (1998).
Ha, "Single-molecule fluorescence resonance energy transfer", Methods, vol. 25, pp. 78-86 (2001).
Ha et al., "Probing the interaction between two single molecules: fluorescence resonance energy transfer between a single donor and a single acceptor", Proc. Natl. Acad. Sci. USA, vol. 93, pp. 6264-6268 (1996).
Ha et al., "Ligand-induced conformational changes observed in single RNA molecules", Proc. Natl. Acad. Sci. USA, vol. 96, pp. 9077-9082 (1999).
Harms et al., "Single-molecule imaging of L-type Ca(2+) channels in live cells", Biophys. J., vol. 81, pp. 2639-2646 (2001).
Heinze et al., "Simultaneous two-photon excitation of distinct labels for dual-color fluorescence crosscorrelation analysis", Proc. Natl. Acad. Sci. USA, vol. 97, No. 19, pp. 10377-10382 (2000).

(56) References Cited

OTHER PUBLICATIONS

Hobohm et al., "Is the circadian clock of gonyaulax held stationary after a strong pulse of anisomycin?", Comp. Biochem. Physiol., vol. 79, No. 3, pp. 371-378 (1984).
Ilegems et al., "Monitoring mis-acylated tRNA suppression efficiency in mammalian cells via EGFP fluorescence recovery", Nucleic Acids Res., vol. 30, No. 23, e128 (2002).
Jaiswal et al., "Long-term multiple color imaging of live cells using quantum dot bioconjugates", Nat. Biotechnol., vol. 21, p. 47-51 (2003).
Jovin, "Quantum dots finally come of age", Nat. Biotechnol., vol. 21, pp. 32-33 (2003).
Jun et al, "Fluorescent labeling of cell-free synthesized proteins with fluorophore-conjugated methionylated tRNA derived from in vitro transcribed tRNA", J Microbiol Methods, vol. 73, pp, 247-251 (2008).
Kenworthy, "Imaging protein-protein interactions using fluorescence resonance energy transfer microscopy", Methods, vol. 24, pp. 289-296 (2001).
Klostermeier, "RNA conformation and folding studied with fluorescence resonance energy transfer", Methods, vol. 23, pp. 240-254 (2001).
Lee et al., "Single-molecule four-color FRET", Angew Chem. Int. Ed. Engl., vol. 49, pp. 9922-9925 (2010).
Loy et al., "probeBase: an online resource for rRNA-targeted oligonucleotide probes", Nucleic Acids Res., vol. 31, No. 1, pp. 514-516 (2003).
Medintz et al., "Self-assembled nanoscale biosensors based on quantum dot FRET donors", Nat. Mater., vol. 2, pp. 630-638 (2003).
Meissner et al., "Development of an inducible pol III transcription sytem essentially requiring a mutated form of the TATA-binding protein", Nucleic Acids Res., vol. 29, No. 8, pp. 1672-1682 (2001).
Miyawaki et al., "Lighting up cells: labelling proteins with fluorophores", Nat. Cell. Biol. Suppl. S1-S7 (2003).
Muralikrishna et al., "A photolabile oligodeoxyribonucleotide probe of the decoding site in the small subunit of the *Escherichia coli* ribosome: identification of neighboring ribosomal components", Biochemistry, vol. 33, pp. 1392-1398 (1994).
Odom et al., "Fluorescence labeling and isolation of labeled RNA and ribosomal proteins", Methods Enzymol., vol. 164, pp. 174-187 (1988).
Odom et al., "Relaxation time, interthiol distance, and mechanism of action of ribosomal protein S1", Arch. Biochem. Biophys., vol. 230 No. 1, pp. 178-193 (1984).
Odom et al., "Distances between 3' ends of ribosomal ribonucleic acids reassembled into *Escherichia coli* ribosomes", Biochemistry, vol. 19, No. 26, pp. 5947-5954 (1980).
Olejnik et al, "N-terminal labeling of proteins using initiator tRNA", Methods, vol. 36, pp. 252-260 (2005).
Paulsen et al., "Topological arrangement of two transfer RNAs on the ribosome. Fluorescence energy transfer measurements between A and P site-bound tRNAPHE", J. Mol. Biol., vol. 167, pp. 411-426 (1983).
Pelletier et al., "The involvement of mRNA secondary structure in protein synthesis", Biochem. Cell. Biol., vol. 65, pp. 576-581 (1987).
Plumbridge et al., "Characterisation of a new, fully active fluorescent derivative of *E. coli* tRNAPHE.", Nucleic Acids Res., vol. 8, No. 4, pp. 827-843 (1980).
Robbins at al., "Comparison of ribosomal entry and acceptor transfer ribonucleic acid binding sites on *Escherichia coli* 70S ribosomes. Fluorescence energy transfer measurements from Phe-tRNAPHE to the 3' end of 16S ribonucleic acid", Biochemistry, vol. 22, pp. 5675-5679 (1983).
Sako et al., "Total internal reflection fluorescence microscopy for single-molecule imaging in living cells", Cell Struct. Funct., vol. 27, pp. 357-365 (2002).
Sako et al., "Single-molecule visualization in cell biology", Nat. Rev. Mol. Cell. Biol. Suppl. SS1-SS5 (2003).
Santoro et al., "An efficient system for the evolution of aminoacyl-tRNA synthetase specificity", Nat. Biotechnol., vol. 20, pp. 1044-1048 (2002).
Schlegel et al., "The turnover of tRNAs microinjected into animal cells", Nucleic Acids Res., vol. 5, No. 10, pp. 3715-3729 (1978).
Schwille, "Analyzing single protein molecules using optical methods", Curr. Opin. Biotechnol., vol. 12, pp. 382-386 (2001).
Sei-Lida et al., "Real-time monitoring of in vitro transcriptional RNA synthesis using fluorescence resonance energy transfer", Nucleic Acids Res., vol. 28, No. 12, e59 (2000).
Selvin, "The renaissance of fluorescence resonance energy transfer", Nat. Struct. Biol., vol. 7, No. 9, pp. 730-734 (2000).
Shimizu et al., "Cell-free translation reconstituted with purified components", Nat. Biotechnol., vol. 19, pp. 751-755 (2001).
Singh et al., "Rapid kinetic characterization of hammerhead ribozymes by real-time monitoring of fluorescence resonance energy transfer (FRET)", RNA, vol. 5, pp. 1348-1356 (1999).
Smilansky, "Automatic registration for images of two-dimensional protein gels", Electrophoresis, vol. 22, pp. 1616-1626 (2001).
Stapulionis et al., "A channeled tRNA cycle during mammalian protein synthesis", Proc. Natl. Acad. Sci. USA, vol. 92, pp, 7158-7161 (1995).
Surrey et al., "Chromophore-assisted light inactivation and self-organization of microtubules and motors", Proc. Natl. Acad. Sci. USA, vol. 95, pp. 4293-4298 (1998).
Sytnik et al., "Peptidyl transferase center activity observed in single ribosomes", J. Mol. Biol., vol. 285, pp. 49-54 (1999).
Terpe, "Overview of tag protein fusions: from molecular and biochemical fundamentals to commercial systems", Appl. Microbiol. Biotechnol. vol. 60, pp. 523-533 (2003).
Thompson et al., "Recent advances in fluorescence correlation spectroscopy", Curr. Opin. Struct. Biol., vol. 12, pp. 634-641 (2002).
Toomre et al., "Lighting up the cell surface with evanescent wave microscopy", Trends Cell. Biol., vol. 11, pp. 298-303 (2001).
Tsuji et al., "Direct observation of specific messenger RNA in a single living cell under a fluorescence microscope", Biophys. J., vol. 78, pp. 3260-3274 (2000).
Vanzi et al., "Protein synthesis by single ribosomes", RNA, vol. 9, pp, 1174-1179 (2003).
Wolin et al., "Ribosome pausing and stacking during translation of a eukaryotic mRNA", EMBO J., vol. 7, No. 11, pp. 3559-3569 (1988).
Zhuang et al., "Correlating structural dynamics and function in single ribozyme molecules", Science, vol. 296, pp. 1473-1476 (2002).
Zipfel et al., "Nonlinear magic: multiphoton microscopy in the biosciences", Nat. Biotechnol., vol. 21, No. 11, pp. 1369-1377 (2003).
Amann, Rudolf I. et al., (1995) "Phylogenetic identification and in situ detection of individual microbial cells without cultivation". Microbiol Rev. vol. 59(1), pp. 143-169.
Bakin, A. V. et al., (1991) "Spatial organization of template polynucleotides on the ribosome determined by fluorescence methods". J Mol Biol., vol. 221(2), pp. 441-453.
Behrens, Sebastian et al, (2003) "Is the in situ accessibility of the 16S rRNA of *Escherichia coli* for Cy3-labeled oligonucleotide probes predicted by a three-dimensional structure model of the 30S ribosomal subunit?" Appl Environ Microbiol, vol. 69(8), pp. 4935-4941.
Dirks, Roeland W. et al., (2001) "Methods for visualizing RNA processing and transport pathways in living cells". Histochemistry and Cell Biology, vol. 115(1), pp. 3-11.
Felgner, Philip L. et al., (1987) "Lipofection: a highly efficient, lipid-mediated DNA-transfection procedure". Proc Natl Acad Sci USA, vol. 84(21), pp. 7413-7417.
Fuchs, Bernhard M. et al, (2001) "In situ accessibility of *Escherichia coli* 23S rRNA to fluorescently labeled oligonucleotide probes". Appl Environ Microbiol., vol. 67(2), pp. 961-968.
Ha, T. (2001) "Single Molecules", vol. 2(4); pp. 283-284 (abstract).
Hanley, Q. S. et al., (1999) "An optical sectioning programmable array microscope implemented with a digital micromirror device". J Microsc., vol. 196, pp. 317-331.
Jia, Y. et al., (1997) "Nonexponential kinetics of a single tRNA$^{Phe}$ molecule under physiological conditions". Proc Natl Acad Sci USA, vol. 94(15), pp. 7932-7936.

(56) References Cited

OTHER PUBLICATIONS

Kukhanova, M. K. et al., (1974) "Peptidyl-tRNA with a fluorescent label: Ribosome substrates in peptide bond formation". Molecular Biology Reports, vol. 1(7), pp. 397-400.

Laursen, Brian Sogaard et al., (2005) "Initiation of protein synthesis in bacteria". Microbiol Mol Biol Rev., vol. 69(1), pp. 101-123.

Liu, Wei-Yi et al., (2005) "Efficient RNA interference in zebrafish embryos using siRNA synthesized with SP6 RNA polymerase". Dev Growth Differ., vol. 47(5), pp. 323-331.

Malone, Robert W. et al., (1989) "Cationic liposome-mediated RNA transfection". Proc Natl Acad Sci USA., vol. 86(16), pp. 6077-6081.

Mascarenhas, Judita et al., (2001) "Specific polar localization of ribosomes in *Bacillus subtilis* depends on active transcription". EMBO Rep., vol. 2(8), pp. 685-689.

Odom, O. W. et al., (1990) "Movement of tRNA but not the nascent peptide during peptide bond formation on ribosomes". Biochemistry, vol. 29(48), pp. 10734-10744.

Palakurthi, Sangeetha S. et al., (2001) "Anticancer effects of thiazolidinediones are independent of peroxisome proliferator-activated receptor gamma and mediated by inhibition of translation initiation". Cancer Res., vol. 61(16), pp. 6213-6218.

Paulsen, Harald and Wintermeyer, Wolfgang (1986) "tRNA topography during translocation: steady-state and kinetic fluorescence energy-transfer studies". Biochemistry, vol. 25(10), p. 2749.

Sakamoto, T. et al., (2004) "Improvement of dermatitis by iontophoretically delivered antisense oligonucleotides for interleukin-10 in NC/Nga mice". Gene Ther., vol. 11(3), pp. 317-324.

Sako, Yusuke et al., (2006) "A novel therapeutic approach for genetic diseases by introduction of suppressor tRNA". Nucleic Acids Symp. Ser., vol. 50, pp. 239-240.

Schwille, Petra et al., (1999) "Molecular Dynamics in Living Cells Observed by Fluorescence Correlation Spectroscopy with One- and Two-Photon Excitation". Biophysical Journal, vol. 77(4), pp. 2251-2265.

Seibel, Peter et al., (1995) "Transfection of mitochondria: strategy towards a gene therapy of mitochondrial DNA diseases". Nucleic Acids Res. vol. 23(1), pp. 10-17.

Szollosi, Janos et al., (1998) "Application of fluorescence resonance energy transfer in the clinical laboratory: routine and research". Cytometry, vol. 34(4), pp. 159-179.

Watson, Bonnie S. et al., (1995) "Macromolecular arrangement in the aminoacyl-tRNA.elongation factor Tu.GTP ternary complex. A fluorescence energy transfer study". Biochemistry, vol. 34(24), pp. 7904-7912.

Weiss, Shimon (1999) "Fluorescence spectroscopy of single biomolecules". Science, vol. 283(5408), pp. 1676-1683.

Welch, Ellen M. et al., (2007) "PTC124 targets genetic disorders caused by nonsense mutations". Nature, vol. 447(7140), pp. 87-91.

Wiseman, Paul W. and Petersen, Nils O. (1999) "Image Correlation Spectroscopy. II. Optimization for Ultrasensitive Detection of Pre-existing Platelet-Derived Growth Factor-b Receptor Oligomers on Intact Cells". Biophysical Journal, vol. 76(2), pp. 963-977.

Yonath, Ada (2005) "Antibiotics targeting ribosomes: resistance, selectivity, synergism and cellular regulation". Annu Rev Biochem., vol. 74, pp. 649-679.

International Search Report and Written Opinion for PCT/IL2008/001328 mailed Mar. 30, 2009.

\* cited by examiner

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
tatcagcgtg ccttctcc                                                  18

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
tatcagcgtg ccttctcc                                                  18

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
tatcagcgtg ccttctcc                                                  18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
tatcagcgtg ccttctcc                                                  18

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgacgttyta aacccagctc                                                20

<210> SEQ ID NO 6
<211> LENGTH: 18
<212> TYPE: DNA
<213> ORGANISM: Artificial Sequence
```

```
-continued

<220> FEATURE:
<223> OTHER INFORMATION: Synthetic

<400> SEQUENCE: 6
aaagtggtaa gcgccctc                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
accccagtca tgaatcac                                                 18

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
agccgttacc ccaccta                                                  17

<210> SEQ ID NO 9
<211> LENGTH: 18
<212> TYPE: DNA
<213> ORGANISM: Artificial Sequence
<220> FEATURE:
<223> OTHER INFORMATION: Synthetic

<400> SEQUENCE: 9
gctgcctccc gtaggagt                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
aagctaccta cttcttt                                                  18
```

SYSTEMS AND METHODS FOR MEASURING TRANSLATION ACTIVITY IN VIABLE CELLS

This application is a 371 filing of International Patent Application PCT/IL2008/001328 filed Oct. 7, 2008, which claims the benefit of application Nos. 60/978,420 filed Oct. 9, 2007 and 61/086,165 filed Aug. 5, 2008.

FIELD OF THE INVENTION

The present invention relates to translation systems and methods for measuring translation activity. In particular, the present invention relates to real-time measurement of general ribosomal activity in viable cells and organelles.

BACKGROUND OF THE INVENTION

The Process of Protein Synthesis

Protein synthesis is one of the most central life processes. A protein is formed by the linkage of multiple amino acids via peptide bonds, according to a sequence defined by the template messenger RNA (mRNA). Protein synthesis occurs in the ribosomes, the protein manufacturing plants of every organism and nearly every cell type.

Ribosomes are ribonucleoprotein particles consisting of a small and large subunit. In bacteria these subunits have sedimentation coefficients of 30 and 50, and thus are referred to as "30S" and "50S" respectively; in eukaryotes the sedimentation coefficients are 40 and 60. The translation system makes use of a large number of components, including inter alia the ribosome, initiation, elongation, termination and recycling factors, transfer RNA, amino acids, aminoacyl synthetases, magnesium, and the product polypeptides.

tRNAs are 73-93 nucleoside RNA molecules that recruit amino acid residues to the protein synthesis machinery. The structure of tRNA is often depicted as a cloverleaf representation. Structural elements of a typical tRNA include an acceptor stem, a D-loop, an anticodon loop, a variable loop and a TψC loop. Aminoacylation, or charging, of tRNA results in linking the carboxyl terminal of an amino acid to the 2'-(or 3'-) hydroxyl group of a terminal adenosine base via an ester linkage. Aminoacylation occurs in two steps, amino acid activation (i.e. adenylation of the amino acid to produce aminoacyl-AMP), tRNA aminoacylation (i.e. attachment of an amino acid to the tRNA).

Protein translation, also referred to as "polypeptide synthesis," begins by formation of the initiation complex, composed of the two ribosomal subunits, proteins known as "initiation factors," mRNA, and an initiator tRNA, which recognizes the base sequence UAG, i.e. the initiator codon of open reading frames. Initiation factors are proteins whose function is to bring the mRNA and initiator tRNA to the ribosome. The initiation factors first bind to the small ribosome subunit, then to the initiator tRNA, and then the large ribosomal subunit is recruited. Elongation proceeds with repeated cycles of charged tRNAs binding to the ribosome (a step termed "recognition"), peptide bond formation, and translocation. Elongation factors recruit and assist with binding of additional tRNAs and in elongation of the polypeptide chain. Elongation utilizes enzymes such as peptidyl transferase, which catalyzes addition of amino acid moieties onto the growing chain. Termination factors recognize a stop signal, such as the base sequence UGA, in the mRNA, terminating polypeptide synthesis and releasing the polypeptide chain and mRNA from the ribosome (Kapp et al., 2004, Annu Rev Biochem. 73:657-704). After termination of translation, the recycling factor enables the ribosome to dissociate into its two separate subunits, which are then available for a new round of protein synthesis.

In eukaryotes, ribosomes are often attached to the membranes of the endoplasmic reticulum (ER) and Golgi compartments. Additionally, ribosomes are active in organelles such as endoplasmic reticulum and mitochondria and, in plant cells, in chloroplasts, and other subcellular compartments. One important locus of protein synthesis activity is the dendritic spines of neurons.

Ribosomes as Targets of Drugs and Antibiotic Compounds

There are variations between eukaryotic and prokaryotic translation mechanisms, as well as subtler differences between eukaryotic ribosomes in different organisms and subcellular components. Prokaryotic ribosomes are the targets of many antibiotic compounds (Yonath, Annu Rev Biochem. 74:649-79, 2005; Hainrichson M et al, Designer aminoglycosides: the race to develop improved antibiotics and compounds for the treatment of human genetic diseases. Org Biomol Chem 6 (2):227-39, 2008). Such antibiotics must not exhibit significant inhibition of eukaryotic ribosomes, including mitochondrial ribosomes, and thus may exploit subtle differences between prokaryotic vs. mammalian and mitochondrial ribosomes. Widespread use of antibiotics over the past half-century has lead to emergence of bacterial strains resistant to many antibiotics now in use.

For these reasons, fast and accurate measurement of ribosomal activity is important for development of new types of antibiotics, including activity of mitochondrial ribosomes in the context of an intact eukaryotic cell, in order to produce new antibiotics to combat the increasing number of the antibiotic-resistant strains (Cohen, 1992, Science, 257: 1050-1055). Use of these assays may lead to the discovery of new classes of antibiotics that are toxic to a broad range of pathogenic bacteria, and at the same time, harmless to their mammalian hosts.

Diseases Related to Protein Translation

Control of protein translation is implicated in a large number of diseases. For example, a family of central nervous system (CNS) disorders connected with protein synthesis disturbances in neural spines is currently the subject of intense research. The family includes fragile X mental retardation, autism, aging and memory degeneration disorders such as Alzheimer's disease. Neural spines and synapses contain their own protein synthesis machinery. Synaptic plasticity, underpinning the most basic neural functions of memory and learning, is dependent upon proper regulation of spinal protein synthesis. Memory and aging are hypothesized to be linked to this phenomenon; fragile-X mental retardation and autism are known to be.

Fragile-X syndrome is the most common form of inherited mental retardation in humans. Conditions associated with the syndrome include mild to moderate cognitive abnormalities and behavioral disorders similar to autism, attention deficit disorder, obsessive-compulsive tendencies, hyperactivity, slow development of motor skills, and anxiety/fear disorder. Fragile X syndrome results from a deficiency of the fragile X mental retardation protein, FMRP, which is encoded by the X-linked FMR1 gene, usually due to transcriptional silencing of this gene brought about by the expansion and hypermethylation of a $(CGG)_n$ trinucleotide repeat in the 5' untranslated region (UTR) of the gene, indicating that the necessity of FMRP for higher cognitive function. In the cytoplasm, FMRP-mRNP is normally associated with translating polyribosomes. In dendrites, FMRP is believed to modulate translation of mRNAs and acts as a translational suppressor.

Another important family of diseases directly connected to protein synthesis includes genetic disorders associated with the presence of premature termination codons (PTC) in the coding sequence of a critical protein, preventing its translation. Such diseases include Duchenne Muscular Dystrophy and a large family of congenital diseases. A small molecule known as PTC124 (Welch E M et al, Nature 2007 May 3; 447(7140):87-91) helps the ribosome slide over the mutated codon, thereby producing the required protein, albeit at only at 1-5% of normal concentrations. These amounts are often sufficient to sustain the life of an afflicted individual. PTC suppression has also been achieved by introducing charged suppressor tRNA into a living cell, enabling readthrough suppression of the PTC-containing mRNA and accumulation of the encoded protein (Sako et al, Nucleic Acids Symp Ser, 50:239-240, 2006.

Other diseases believed to be connected to control of protein synthesis include cardiac hypertrophy, restenosis, diabetes and obesity. Inflammatory bowel disease (e.g., ulcerative colitis and Crohn's disease) is associated with increased whole-body protein turnover. Reduced translational activity in cells, tissues, organs and organisms is a widely observed age-associated biochemical change. The consequences of slower rates of protein synthesis are manifold in the context of aging and age-related pathology. These include decreased availability of enzymes, inefficient removal of intracellular damaged substances, inefficient intra- and intercellular communication, decreased production of hormones and growth factors, decreased production of antibodies, and altered nature of the extracellular matrix.

In addition, control of protein synthesis is often compromised by cellular transformation. Novel anticancer drugs capable of targeting the ribosome in cancer cells are currently being developed (Palakurthi, S. S. et al., Cancer Research 61: 6213-6218, 2001).

Mitochondria-Related Diseases

Mitochondria found in eukaryotic cells have transcription and translation systems for expression of the endogenous mitochondrial DNA (mtDNA) that use a genetic code different from the universal code used by nuclear genomic DNA. Most mitochondrial proteins are encoded by nuclear DNA that is transcribed, translated in the cytosol, and imported into the mitochondria. However, some mitochondrial proteins are transcribed from mtDNA and translated within the organelle itself, using the mitochondrial system that includes two ribosomal RNA and 22 tRNAs. The human mitochondrial DNA (mtDNA) consists of 37 genes (Wallace, Gene. 354:169-80, 2005). The mitochondrial DNA encodes proteins that are essential components of the mitochondrial energy generation pathway, oxidative phosphorylation (OXPHOS). Oxidative phosphorylation generates heat to maintain body temperature and ATP to power cellular metabolism. Mitochondria also produce a significant fraction of cellular reactive oxygen species (ROS) and can initiate apoptosis through activation of the mitochondrial permeability transition pore (mtPTP) in response to energy deficiency and oxidative damage. Mitochondrial ROS cause mutation of mtDNA, which has been associated with a wide range of age-related diseases including neurodegenerative diseases, cardiomyopathy, metabolic diseases such as diabetes, and various cancers.

FRET, Quenching Pairs, and FCS

Fluorescence resonance energy transfer (FRET) is a method widely used to monitor biological interactions. FRET utilizes a donor fluorophore, having an emission spectrum that overlaps with the excitation spectrum of the acceptor fluorophore. Only when the donor fluorophore and acceptor fluorophore are in close proximity, typically about 10 nm, is a signal emitted from the acceptor fluorophore. FRET is described in Szöllosi J, Damjanovich S, Mátyus L, Application of fluorescence resonance energy transfer in the clinical laboratory: routine and research, Cytometry 34 (4):159-79, 1998. A quenching pair is a fluorophore in combination with a second molecule that quenches fluorescence of the fluorophore when in close proximity thereto. Thus, when the quenching pair is separated, under conditions wherein the fluorophore emits radiation, a signal is emitted.

Fluorescent Correlation Spectroscopy (FCS) is described for example in Schwille et al., Biophysical Journal, Vol. 77, 1999: 2251-2265; Wiseman and Petersen, Biophysical Journal, Vol. 76, 1999: 963-977; and Thompson et al., Current Opinion in Structural Biology, 2002, 12:634-641. In this method, signal variation is measured and used for computing basic parameters of the system, such as the number of fluorescing molecules in the system. The variability is mainly a function of molecules entering and leaving the illuminated volume.

Existing Methods of Measuring Protein Translation

Methods current used in the art typically comprise radioactive labeling of amino acid residues, following by electrophoretic separation of the protein mixture and detection of radioactive label. Such methods produce an estimation of the total production of proteins over a given period of time measured in minute, hours or days, as opposed to the instant readout of methods of the present invention. Current methods do not provide real-time measurements of the ribosomal activity, nor can they identify subcellular localization of protein synthesis or measure the dynamics of this activity.

U.S. Pat. No. 6,210,941 discloses methods for the non-radioactive labeling, detection, quantitation and isolation of nascent proteins translated in a cellular or cell-free translation system. tRNA molecules are mis-aminoacylated with non-radioactive markers that may be non-native amino acids, amino acid analogs or derivatives, or substances recognized by the protein synthesizing machinery. These methods require elaborate and expensive cell preparations and equipment to enable isolation of nascent proteins, and are not suitable as a simple tool for measuring general protein synthesis rates in live cells or organelles, particularly in real time.

U.S. Patent application Nos. 2003/0219783 and 2004/0023256 of Puglisi disclose compositions and methods for solid surface translation, where translationally competent ribosome complexes are immobilized on a solid surface. The ribosomes may be labeled to permit analysis of single molecules for determination of ribosomal conformational changes and translation kinetics. One or more components of the ribosome complex may be labeled at specific positions, and arrays of ribosome complexes may comprise a panel of different labels and positions of labels. Monitoring may comprise co-localization of fluorescently-labeled tRNA with fluorescently-labeled ribosomes or fluorescence resonance energy transfer (FRET) between a labeled ribosome and separately labeled mRNA. However, only cell-free translation methods are disclosed; methods for measuring overall cellular translation activity, in real time in viable cells or organelles, are neither disclosed nor suggested.

WO2004/050825 of the inventor of the present invention discloses methods for monitoring the synthesis of proteins by ribosomes in cells or a cell-free translation system. WO2005/116252 of the inventor of the present invention discloses methods for identifying proteins synthesized in a cell-free translation system. According to the methods described in these applications, the ribosome is engineered to carry a donor fluorophore, and tRNA, amino acids, and/or another component of the ribosome act as a fluorophore acceptor, via either their natural fluorescent properties or introduction of an engineered acceptor fluorophore. Illumination of ribosomes by a light source during translation excites the donor fluorophores and thereby the acceptor fluorophores whenever these are in sufficient proximity to a donor. One or a small number of ribosomes are typically analyzed in one batch. Neither of these references discloses or suggests the methods of the present invention for measuring overall cellular translation activity, in real time in viable cells or organelles.

There is an ongoing need for methods that provide a measure of overall cellular translation activity, in real time and in viable cells. Methods for measuring changes in protein synthesis rates in response to a drug candidate will be very useful for drug screening and assays for predicting therapeutic activity of candidate drugs. Also highly advantageous would be real-time measurement of ribosomal activity at sub-cellular resolution. The present invention overcomes problems and disadvantages associated with current strategies and provides methods for labeling, detection, and quantitation of general translation activity in real time.

SUMMARY OF THE INVENTION

The present invention provides system and methods for measuring protein translation and methods for real time measurements of overall ribosomal activity in viable cells and subcellular compartments and organelles. The methods of the present invention identify active ribosomes and provide a signal indicating a step of total translation activity, such as the rate of any of the steps of protein translation, namely initiation, elongation, termination and recycling. The methods of the present invention can be utilized for numerous applications, including, but not limited to, test-tube diagnostic assays, macroscopic assays and microscopic assays. Particularly, the methods of the present invention provide readouts of the rate of protein synthesis. The methods of the present invention can be applied in any type of cell such as primary cells and cell lines, with relatively simple intervention in the cellular machinery. In addition, the methods of the invention can be applied in subcellular compartments. Measurement of ribosomal activity is obtained in real time, and can instantly follow changes in rates of protein translation, for example resulting from environmental conditions, such as temperature, or from administration of specific compounds, such as small molecule drug candidates, biotherapeutic agents, or any other substances suspected of affecting protein synthesis. Methods of the present invention thus exhibit advantages for measuring the rate of protein synthesis under normal and diseased conditions, under perturbation such as temperature, chemical and other stimuli, and the dynamics of its response to drugs and drug candidates.

It is to be understood that the present invention is applicable for obtaining a value for total protein synthesis rather than individual protein identification, and is therefore suitable for measurements without requiring inspection of individual cells or single molecules.

According to one aspect, the present invention provides an apparatus for measuring protein translation, comprising a cell or subcellular compartment, wherein the cell or subcellular compartment comprises at least one protein synthesis element the protein synthesis element being labeled with at least one marker, wherein the marker is capable of providing a detectable signal in response to overall translation activity in the cell or subcellular compartment, and wherein said marker is detectable through detection of electromagnetic radiation. In another embodiment, a plurality of cells or subcellular compartments comprising the labeled element is utilized in the apparatus. Each possibility represents a separate embodiment of the present invention.

"Protein synthesis element" as used herein, refers to a macromolecule or a molecular complex involved in any of the phases of protein synthesis by the ribosome, including, but not limited to, a ribosomal protein, ribosome, ribosomal subunit, rRNA, tRNA, animoacyl synthetase, translation factor, amino acid and guanosine triphosphate (GTP). The protein synthesis element may further refer to ternary complexes, such as, GTP-tRNA, elongation factor and the like.

According to one embodiment, the protein synthesis element is a translation factor selected from the group consisting of a preinitiation factor, an initiation factor, an elongation factor, a termination factor, a recycling factor, an amino-acyl synthetase, and a peptidyl transferase. According to some embodiments, said cells are selected from the group consisting of mammalian cells, avian cells, insect cells, bacterial cells, yeast cells and plant cells.

According to other embodiments, said subcellular compartments are selected from the group consisting of dendritic spines, mitochondria, endoplasmic reticulum (ER) and chloroplasts.

According to some embodiments, the marker comprises at least one photo-active component. According to other embodiments, the marker comprises a label selected from the group consisting of a fluorescent dye, a donor-quencher pair and a fluorescent donor-acceptor pair. In another embodiment, the marker is a label selected from the group consisting of a fluorescent dye, a donor-quencher pair and a fluorescent donor-acceptor pair.

According to one embodiment, said radiation comprises radiation obtained by energy transfer between said labeled protein synthesis element and at least another labeled protein synthesis element. In another embodiment, the radiation emanates from said labeled protein synthesis element and at least another labeled protein synthesis element. Each possibility represents a separate embodiment of the present invention.

In another embodiment, the electromagnetic radiation detected in the present invention is detectable by the method of anisotropy microscopy. In another embodiment, an apparatus of the present invention further comprises a microscope suitable for anisotropic evaluation. Each possibility represents a separate embodiment of the present invention.

According to another embodiment, said radiation comprises a signal selected from a FRET signal, a quenching signal and a fluorescent signal.

According to another embodiment, the signal indicates a parameter selected from the group consisting of: the rate of a step of protein synthesis, the ratio of immobilized tRNAs to freely diffusing tRNAs, the ratio of functional initiation complexes to separate factors of the initiation complex, the ratio of functional elongation factor complexes to separate factors of the elongation complex, the ratio of assembled to separate ribosomal subunits, the ratio of separate to assembled initiation or pre-initiation complex, and the ratio of separate to assembled ternary complexes.

According to another embodiment, the signal indicates the rate of a specific step of protein synthesis selected from the group consisting of: initiation, elongation, termination and recycling.

According to another embodiment, the labeled protein synthesis element is a ribosome or a subunit thereof, and said signal indicates the ratio of intact ribosomes to separated small and large ribosomal subunits. According to another embodiment, the protein synthesis element is a ribosome or a subunit thereof, and the marker is a fluorescent-tagged oligonucleotide DNA marker.

According to another embodiment, the subunit is selected from the group consisting of the large ribosomal unit (50S) and the ribosomal small subunit (30S).

According to a further aspect, the present invention provides a method for measuring protein translation activity, the method comprising the steps of:
(i) labeling at least one protein synthesis element with at least one marker detectable through detection of electromagnetic radiation;
(ii) introducing into a biological sample the at least one labeled protein synthesis element, wherein the marker produces electromagnetic radiation in response to translation activity in the biological sample, wherein the biological sample is selected from the group consisting of a cell and a subcellular compartment; and
(iii) detecting the electromagnetic radiation or signals produced by same,
thereby measuring protein translation activity.

In another embodiment, a method of the present invention further comprises the step of analyzing said signals, thereby obtaining an estimate of overall translation activity. In another embodiment, a plurality of cells or subcellular compartments is utilized in the method. In another embodiment, analysis of the signal produces a readout of a parameter of translation activity. In another embodiment, analysis of the signal produces an estimate of an parameter of overall translation activity. Each possibility represents a separate embodiment of the present invention.

According to another embodiment, the step of analyzing said signals provides a readout of a parameter of overall translation activity selected from the group consisting of: the rate of translational activity, the ratio of labeled versus unlabeled tRNA, and the average translation speed.

According to another embodiment, the step of analyzing comprises the step of computing the number of events (N) over a period of time t, as defined hereinbelow, thereby obtaining an estimate of the rate of overall translational activity.

According to one embodiment, the method of the present invention further comprises the step of irradiating the apparatus or biological sample with a source of electromagnetic radiation prior to the step of detecting the electromagnetic radiation. This source produces electromagnetic radiation of a different wavelength than that detected as a readout of protein translation activity. In another embodiment, the wavelength of electromagnetic radiation produced by this source is the excitation wavelength of a marker of the present invention. In another embodiment, the wavelength is the excitation wavelength of the donor fluorophore of the FRET pair used to label 2 components of the translational machinery. In another embodiment, the wavelength is the excitation wavelength of the donor fluorophore of a quenching pair. Each possibility represents a separate embodiment of the present invention.

According to another embodiment, a method of the present invention further comprises the step of computing the number of events (N) over a period of time t, wherein $$N \sim \frac{\sum I_t^2}{\sum \delta I_t^2}$$

wherein $I_t$ is the average signal strength at time t and $\delta I_t$ is the average signal deviation at time t. "Average signal deviation" refers, in another embodiment, to the detected signal minus the average signal.

According to another embodiment, the biological samples of methods of the present invention are selected from the group consisting of whole cells and subcellular compartments.

According to some embodiments, a method of the present invention further comprises the step of detecting the electromagnetic radiation and comparing the amount of radiation to a reference standard. In another embodiment, a level of radiation significantly different from the reference standard is indicative of a disease or disorder. In another embodiment, the step of detecting said electromagnetic radiation is diagnostic for a disease, disorder or pathological condition. In another embodiment, the step of analyzing said electromagnetic radiation is diagnostic for a disease, disorder or pathological condition. Thus, methods of the present invention can be used to detect in a subject a condition selected from the group consisting of a disease, a disorder and a pathological condition.

According to one embodiment, the condition is selected from the group consisting of fragile X, mental retardation, autism, aging and memory degeneration.

According to another embodiment, the disease is selected from the group consisting of a mitochondria-related disease, cardiac hypertrophy, restenosis, diabetes, obesity, a genetic disease related to a premature termination codon (PTC), and inflammatory bowel disease.

In another embodiment, a method of the present invention further comprises the step of administering to the cultured cells or subcellular compartments at least one drug candidate prior to detecting the electromagnetic radiation signals. According to another embodiment, the method further comprises the step of performing the steps of the above method on a separate biological sample, wherein said separate biological sample is substantially identical to the biological sample analyzed following contact with the drug candidate, except that the separate biological sample has not been contacted with the drug candidate. "Substantially identical" as used herein refers to the absence of apparent differences between the biological samples. A non-limiting example of biological samples that are substantially identical are two different aliquots from the same preparation of cells or subcellular organelles. Each possibility represents a separate embodiment of the present invention.

In another embodiment, the above method further comprises the step of comparing the quantities of electromagnetic radiation obtained from the two biological samples, i.e. those contacted and not contacted with the drug candidate. In another embodiment of this method, a difference between these two quantities indicates that the drug candidate affects protein translation. Each possibility represents a separate embodiment of the present invention.

According to another embodiment, a method of the present invention further comprises the steps of (a) administering to the biological sample a drug candidate; (b) detecting the electromagnetic radiation signals emitted by the biological sample, as described herein; and (c) comparing the electromagnetic radiation signals detected prior to introduction of the drug candidate, vs. the signals detected in the presence of the drug candidate, thereby evaluating the effect of the drug candidate on protein translation.

In another embodiment, the translation apparatus of the present invention is used for high-throughput-screening (HTS) of putative translation modulators.

According to another embodiment, the drug candidate of the present invention is selected from the group consisting of a small molecule, a peptide, an enzyme, a hormone, a biotherapeutic agent, and an antibiotic.

"Biotherapeutic agent," as used herein, refers to a protein, enzyme, metabolite, nucleic acid, or microorganism that has therapeutic characteristics. Biotherapeutic agents originate from nature but can be engineered to produce optimal therapeutic value. The term includes synthetic mimics of naturally occurring proteins, enzymes, metabolites, nucleic acids, and microorganisms. Each possibility represents a separate embodiment of the present invention.

According to another embodiment, the protein synthesis element is selected from the group consisting of a ribosome and a ribosomal subunit, wherein the marker is a fluorescent-tagged oligonucleotide DNA marker.

According to another embodiment, the biological samples are subcellular compartments. According to another embodiment, the biological samples are mitochondria and the protein synthesis element is mitochondria-specific tRNA.

These and other embodiments of the present invention will become apparent in conjunction with the figures, description and claims that follow.

BRIEF DESCRIPTION OF THE INVENTION

The invention is herein described, by way of example only, with reference to the accompanying figures. With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the figures making apparent to those skilled in the art how the several forms of the invention may be embodied in practice.

FIG. 1 is a schematic presentation of a bacterial ribosome structure with the large (50S) subunit 20, small (30S) subunit 25, aminoacyl (A) site 50 where the tRNAs are initially docked, peptidyl (P) site 51 where the growing polypeptide chain is docked, and exit (E) site 52 wherefrom the deacylated tRNA is removed once the cycle is complete. On the right side, tRNAs that are still undocked, i.e. 40, 41, 42 and 43, are depicted. These are charged (ellipse at the top, 32, 33, 40-43) or uncharged (34); and are either not labeled (40, 43), or labeled with donor (33, 34, 42) or with acceptor (32, 41). The labels are shown attached to the D-loop of the tRNA. mRNA being decoded 30 and the nascent polypeptide chain being synthesized 45 are also depicted. The ribosome itself is made up of large folded rRNA chains with ribosomal proteins. The large subunit 20 contains two folded rRNAs, known as 23S and 5S. The small subunit 25 contains one folded rRNA, 30S (not shown). On the folded rRNA chains more than 50 ribosomal proteins are docked (not shown). They are customarily denoted by L1, L2 etc. for the approximately 36 ribosomal proteins attached to the large subunit, and by S1, S2 etc. for the approximately 21 ribosomal proteins attached to the small subunit (numbers given are for *E. coli* ribosomes).

Figure 2:
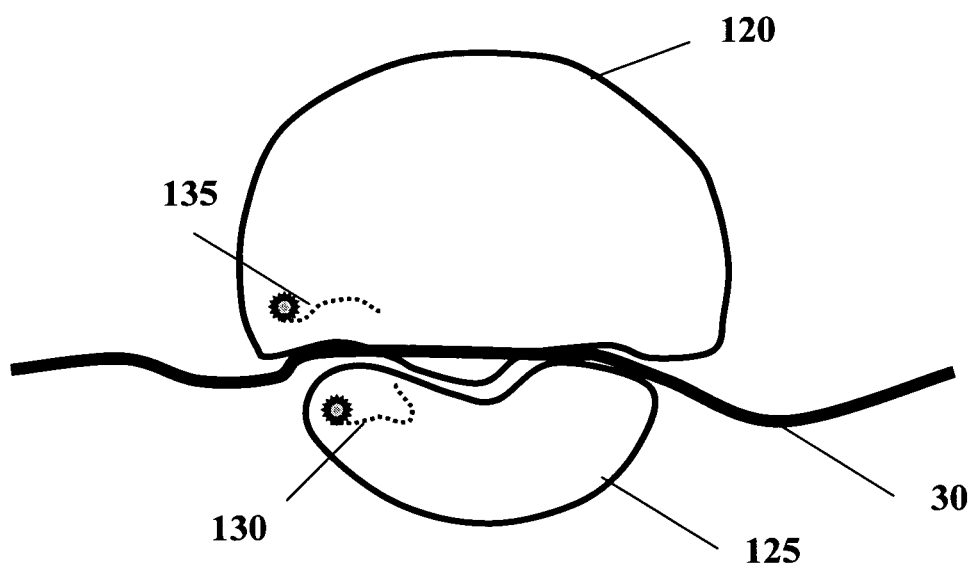

FIG. 2 is a schematic presentation of a ribosome labeled with fluorescent-tagged oligonucleotide DNA (oligoDNA) probes. The donor, a labeled oligoDNA probe 135, is bound to the large subunit 120. The acceptor, a labeled oligoDNA probe 130, is bound to the small subunit 125. The mRNA 30 is also shown. A FRET signal is obtained only from assembled ribosomes.

Figure 3:
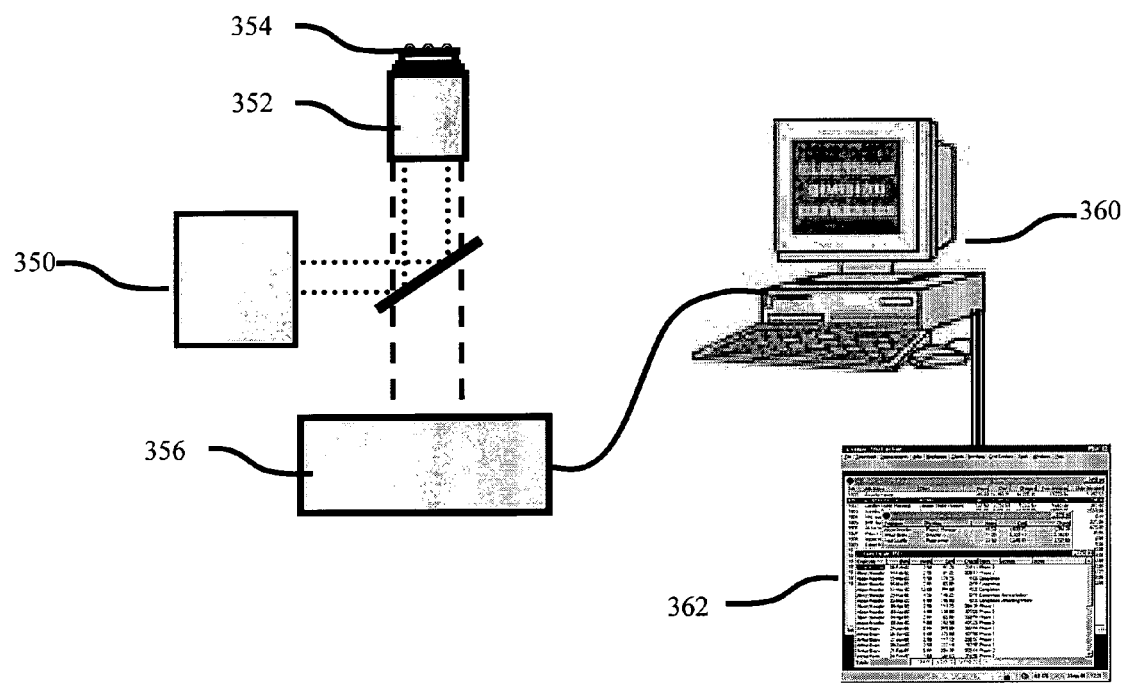

FIG. 3 is an exemplary overview of one preferred embodiment for signal generation and analysis. This example describes a general framework for performing the disclosed assay. Illumination module 350 illuminates sample 354 through microscope 352, and the resulting signals are detected by detection module 356. The resultant image can then be transferred to computerized analysis station 360 which analyzes the images, preferably records the produced signals, and analyzes them to produce an estimation of the specific measurement that is required. The readout can be presented on the computer screen and if desired stored in database 362 for further analysis.

Figure 4:
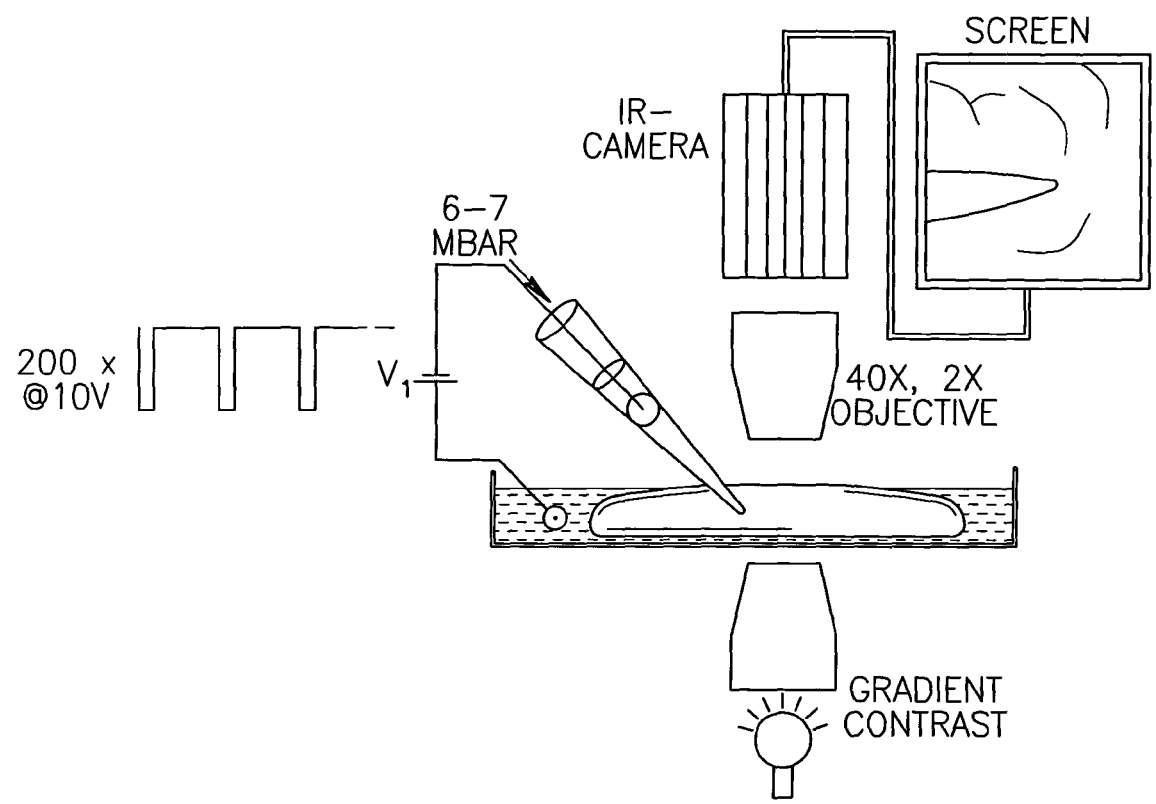

FIG. 4 is an illustration of a modified standard electrophysiology setup used for electroporation-mediated transfection. The culture is placed in a perfusion chamber and visualized using gradient-contrast illumination and IR video microscopy with a 40× water immersion objective and further 2× magnification. Individual neurons can be identified on the monitor screen. The DNA filled micropipette can be targeted precisely to the membrane of a single soma. A back-pressure of 6-7 mbar is applied to the pipette. Two hundred 1 ms-long square pulses with an interpulse delay of 4 ms and an amplitude of 10 V are delivered to each neuron.

DETAILED DESCRIPTION

The present invention provides systems of measuring and monitoring protein translation and methods for measuring general translation activity in viable cells or in specific subcellular compartments. The methods of the present invention can identify active ribosomes, at subcellular resolution, and provide a signal indicating the overall rate of any of the steps of protein synthesis, such as initiation, elongation, termination and recycling, as well as additional steps including recycling, subunit assembly, amino-acid charging onto tRNA, etc.

The present invention can be utilized to obtain a value for overall protein synthesis rather than individual protein identification. For analysis of individual cells and identification of the sequence of individual proteins in individual cells, other methods can be applied.

According to one aspect, the present invention provides an apparatus for measuring protein translation, comprising a cell, wherein the cell comprises at least one protein synthesis element, the protein synthesis element being labeled with at least one marker, wherein the marker is capable of providing a electromagnetic detectable signal in response to overall translation activity in the cell. In another embodiment, a plurality of cells comprising the labeled protein synthesis element is utilized in the apparatus. In another embodiment, the apparatus further comprises instructions for use thereof in measuring or monitoring protein translation in an intact cell. Each possibility represents a separate embodiment of the present invention.

According to the present invention, the protein synthesis element is any macromolecule or molecular complex that may be involved in any of the phases of ribosomal protein synthesis. Such elements include, but not limited to, a ribosomal protein, ribosome, ribosomal subunit, rRNA, tRNA, animoacyl synthetase, translation factor, amino acid and guanosine triphosphate (GTP). The protein synthesis element may further refer to ternary complexes comprising protein synthesis elements, such as, GTP-tRNA, elongation factor and the like.

In another embodiment, the present invention provides an apparatus for measuring protein translation, comprising a subcellular compartment, wherein the subcellular compartment comprises at least one protein synthesis element, the protein synthesis element being labeled with at least one marker, wherein the marker is capable of providing a detectable electromagnetic signal in response to overall translation activity in the subcellular compartment. In another embodiment, a plurality of subcellular compartments comprising the labeled protein synthesis element is utilized in the apparatus. In another embodiment, the apparatus further comprises instructions for use thereof in measuring or monitoring protein translation in a cellular organelle. Each possibility represents a separate embodiment of the present invention.

In another embodiment, the present invention provides a method for measuring translation activity, comprising the steps of:
(i) introducing into cultured cells at least one protein synthesis element, wherein the protein synthesis element is labeled with at least one marker detectable through detection of electromagnetic radiation, wherein the marker is capable of emitting electromagnetic radiation in response to translation activity in the cells or subcellular compartments; and
(ii) measuring electromagnetic radiation signals obtained in response to translation activity. In another embodiment, the method further comprises the step of analyzing said signals, thereby obtaining an estimate of translation activity. Each possibility represents a separate embodiment of the present invention.

In another embodiment, the present invention provides a method for measuring translation activity, comprising the steps of:
(i) introducing into a preparation of a subcellular compartment at least one protein synthesis element, wherein the protein synthesis element is labeled with at least one marker detectable through detection of electromagnetic radiation, wherein the marker is capable of emitting electromagnetic radiation in response to translation activity in the cells or subcellular compartments; and
(ii) measuring electromagnetic radiation signals obtained in response to translation activity. In another embodiment, the method further comprises the step of analyzing said signals, thereby obtaining an estimate of translation activity. Each possibility represents a separate embodiment of the present invention.

In another embodiment, once electromagnetic radiation of the required wavelength and energy has been administered to the biological sample, thereby exciting the donor fluorophores, an optical apparatus monitors fluorescence emanating from the cellular translation system. The acceptor fluorophores on the tRNAs and/or amino acids and/or on the translation factors respond to this energy with the FRET signal whenever a donor and acceptor pair are in sufficient proximity, indicative of particular steps of translation activity. Fluorescent radiation emitted from acceptor fluorophores is detected by the optical apparatus and the event is recorded by the image acquisition device.

"Detectable signal" as used herein refers to a signal able to be detected, over the background level, by standard means of detecting electromagnetic radiation. Means of detecting electromagnetic radiation are well known in the art. In some preferred embodiments, the signal is detected using total internal reflection fluorescence microscopy (TIR-FM) "TIR-FM" as used herein refers to a microscopy illumination method that illuminates a very small volume at the interface of two materials with different refractive indices. TIR-FM is described in WO 05/116252 and in US patent applications 2004/0023256 and 2006/0228708, which are incorporated herein in their entirety by reference.

Additional means of detecting electromagnetic radiation include image acquisition devices; confocal laser scanning microscopes (LSM), used to improve fluorescence image quality by eliminating out-of-focus fluorescence; and spinning disk confocal microscopes, which can include video rate (typically 30 frames per second) imaging with charge-coupled device (CCD) cameras and imaging of 3-dimensional structures in live cells on a subsecond time scale with reduced photobleaching/phototoxicity (Graf et al, Live cell spinning disk microscopy. Adv. Biochem. Eng. Biotechnol. 95: 57-75, 2005). Programmable array microscopes (Hanley et al, An optical sectioning programmable array microscope implemented with a digital micromirror device, J Microsc 196: 317-331, 1999) and line scanning microscopes are available and offer similar advantages to spinning-disk confocals. In addition, multi-photon microscopes use infrared light, which readily penetrates up to 600 μm, allowing deep tissue imaging in living animals (Helmchen and Denk, Deep tissue two-photon microscopy. Nat Methods 2: 932-940, 2005). Additional methods are described inter alia in WO 2007/002758, WO 2008/028298, European Patent EP1428016, and U.S. Pat. No. 7,015,486 and US Patent application 2005/0157294, which are incorporated herein by reference. Each method represents a separate embodiment of the present invention.

As used herein, the term "FRET" ("fluorescence resonance energy transfer") refers to physical phenomenon involving a donor fluorophore and a matching acceptor fluorophore selected so that the emission spectrum of the donor overlaps the excitation spectrum of the acceptor. When donor and acceptor are in close proximity (usually less than 10 nm), excitation of the donor will cause excitation of and emission from the acceptor, as some of the energy passes from donor to acceptor via a quantum coupling effect. Thus, a FRET signal serves as a proximity gauge of the donor and acceptor; only when they are within close proximity is a signal generated.

According to one embodiment, the translation apparatus is placed in a test-tube and manually observed. In another embodiment, the apparatus is placed in a multi-well plate such as a 96 or 384 well plate and observed by a high-throughput fluorimetry instrument.

According to another embodiment, the translation apparatus is placed under a microscope suitable for observing fluorescence at cellular or subcellular resolution, such as instruments available from Zeiss (Oberkochen, Germany) and Leica (Wetzlar, Germany), with an image acquisition device operable at a sufficient rate (10-100 frames per second) and computational units that can acquire and analyze the resulting images and data.

According to another embodiment, the cellular translation apparatus is measured with the technique of anisotropy microscope. Fluorescence anisotropy can distinguish between populations of immobilized fluorophores and freely diffusing (and rotating) fluorophores. The technique can also measure the relative abundance of such populations.

Assessing cellular translation activity can be accomplished in a variety of ways according to methods of the present invention. In one embodiment, a well of a 96 well plate or other commercially available multi-well plate is used to contain the biological sample. In another embodiment, the receptacle is the reaction vessel of a FACS machine. Other receptacles useful in the present invention include, but are not limited to 384 well plates. Still other receptacles useful in the present invention will be apparent to the skilled artisan to facilitate rapid high-throughput screening.

Overview of One Exemplary Embodiment of the Present Invention

One or more moieties of tRNA, amino acid, or translation factor, or a plurality thereof, is engineered to carry a donor fluorophore and utilized as a donor, and another component of the protein translation machinery, or a plurality thereof, is engineered to carry an acceptor fluorophore and utilized as an acceptor. The other component may be similar to, different from, or identical to, the first moiety. The labeled tRNA(s), amino acid(s), translation factor(s) or other labeled components are introduced into cultured cells or subcellular compartments. In order to monitor translation, a light source illuminates the cells, thus exciting the donor fluorophores and thereby the acceptor fluorophores whenever these components are in sufficient proximity to each other, generating a measurable signal.

If the labeled FRET pair, during the process of translation, are brought into close proximity, namely within 10 nm, a FRET signal is observed. When they are separated, the signal ceases. Thus, the level of FRET signals emitted from this pair indicates translation activity. The measurement can be the intensity of the signal or any other relevant feature, such as signal variability, signal polarity, signal lifetime, wavelength, photon number, spectrum, etc. as will be appreciated by one skilled in the art of fluorescent labeling and measurements.

One exemplary measurement measures the variability of the emitted signal. From this variability, it is easy to deduce the number of on/off events in the sample being measured. This is similar to measurements performed in Fluorescent Correlation Spectroscopy (FCS). In these applications, signal variation is measured and used for computing basic parameters of the apparatus, such as the number of fluorescing molecules in the apparatus. In FCS, the variability is mainly a function of molecules entering and leaving the illuminated volume. In an exemplary embodiment of the present invention, the variation is mainly caused by "blinking" (turning on and off) of the signals in response to protein translation activity. Thus, the translation activity being detected is evaluated from the ratio of variation to average signal intensity. Consequently, a signal that does not vary, e.g., in the event that the signal is constantly ON, is interpreted as lack of translation activity.

To compute the number of events, a person skilled in the art can use any suitable method known in the art, including, but not limited to, a method where the signal is measured over a period of time (preferably measured in seconds), and the autocorrelation is computed as follows:

$$N \sim \frac{\sum I_t^2}{\sum \delta I_t^2}$$

where $I_t$ is the signal strength at time t, and $\delta I_N$ is the signal deviation at time t (signal−average signal). In this way of measuring signal variations (with the accepted assumption that blinking follows a Poisson/Gaussian distribution), an estimate can be obtained on the event rate in the observed volume.

Introduction of tRNA and Nucleic Acid Molecules into a Target Cell

According to one embodiment of the present invention, labeled tRNAs are introduced into intact cells. This can be accomplished through a variety of methods that have been previously established such as encapsulation of tRNA into liposomes or vesicles capable of fusion with cells. Fusion introduces the liposome or vesicle interior solution containing the tRNA into the cell. Alternatively, some cells will actively incorporate liposomes into their interior cytoplasm through endocytosis. The labeled tRNAs can also be introduced through the process of cationic detergent mediated lipofection (Feigner et al., Proc. Natl. Acad. Sci. USA 84:7413-17, 1987), or injected into large cells such as oocytes.

Additional methods for introduction of tRNA into a target cell are well known in the art. Such methods include the use of RNAiFect™ from Qiagen of Valencia, Calif. (Sako et al ibid) and electroporation. According to Sako et al, transfection of tRNA molecules, engineered to carry an anticodon for one of the natural stop codons (CUA, UUA, UCA) into A549 cells using the transfection agent RNAiFect™ (Qiagen, Hilden, Germany) is shown. The engineered tRNA were properly transfected and proved functional in a luciferase assay, where the luciferase gene included stop codons UGA, UAA, or UAG in place of the native Ser170 codon.

Additional methods for the introduction of nucleic acid molecules are described in Akhtar et al., (Trends Cell Bio. 2, 139, 1992). WO 94/02595 describes general methods for introduction of enzymatic RNA molecules. These protocols can be utilized for the introduction of virtually any nucleic acid molecule. Nucleic acid molecules can be administered to cells by a variety of methods known to those familiar to the art, including, but not restricted to, encapsulation in liposomes (WO03057164, Malone, R. W. et al., 1989, Proc. Natl. Acad. Sci. USA. 86: 6077-6081; Glenn, J. S. et al., 1993, Methods Enzymol. 221: 327-339; Lu, D. et al., 1994, Cancer Gene Ther. 1: 245-252), by microinjection (Liu et al., 2005, Dev Growth Differ. 47 (5):323-31), by iontophoresis (Sakamoto et al., 2004, Gene Ther. 11 (3):317-24), or by incorporation into other vehicles, such as hydrogels, cyclodextrins, biodegradable nanocapsules, and bioadhesive microspheres.

In another embodiment, INTERFERin™ (Autogen Bioclear™, Wiltshire, UK) is used for tRNA transfection. INTERFERin™ has been successfully used for tRNA transfection U.S. Patent Application No. 2004/235175 discloses a method of inserting RNA into cells. In this method, cells are transfected with RNA using electroporation in order to achieve high transfection efficiency.

In another, non-limiting exemplary electroporation protocol, 3-40×10⁶ cells, preferably growing at log phase, are harvested, counted and washed with cold 1× HeBS (Hepes-buffered saline). Cells are resuspended in 0.8 mL 1× HeBS containing the tRNA and incubated at room temperature for 15 minutes. An exemplary recipe for HeBS is 20 mM HEPES, 150 mM NaCl, pH 7.0-7.4. The tRNA/cell suspension is transferred to an electroporation cuvette and electroporated at an appropriate voltage, preferably at between 500-2000 μF capacitance. The time constant is recorded if desired, and the mixture is optionally incubated in the cuvette for about 10 minutes at room temperature, prior to returning the cells to culture media.

In another, non-limiting exemplary electroporation protocol successfully used for CHO-K1 cells, HEK cells, and rat hippocampal neurons (thus having utility for a large variety of cell types), tRNA is precipitated (either alone or as a coprecipitate with DNA) in ethanol and ammonium acetate at −20° C. for at least 1 hour. The precipitated tRNA is pelleted, vacuum dried, and resuspended in $CO_2$-independent medium to the desired final concentration (4 μg/μl tRNA, either with our without 2.5 μg/μl carrier DNA, is typically appropriate). Immediately prior to electroporation, the media is replaced with $CO_2$-independent media, containing no glutamine, FBS or antibiotics. $CO_2$-independent media are available e.g. from Invitrogen-Gibco and include phenol red free media, Liebovitz's L15 Media (catalogue no. 11415-114), and catalogue nos. 18055-088; 18045-088, and 041-95180M. Approximately 5 µl of electroporation solution is added to the cells, followed by electrical pulse application. For CHO-K1 cells and HEK cells, four 120 V pulses of 50 ms duration are typically used, and for neurons, four 160 V pulses of 25 ms duration. The $CO_2$-independent media is immediately replaced with fresh Ham's F12 media for CHOK1 cells, DMEM for HEK cells, or neurobasal media for neurons, and cells are returned to the 37° C. incubator.

In another, non-limiting exemplary electroporation protocol, electrolyte-filled fused silica capillaries (30 cm long, 30-µm id., 375-µm od) are used. The outlet end of the capillaries is tapered to an approximate outer tip diameter (typically 50 µm, depending on the size of the cell type used). Exemplary electrolytes useful in this method are those based on HEPES buffer. The tapered outlet end of the capillary is submerged in the buffer contained in the cell chamber, and the inlet end is placed in a buffer-filled vial. Both the capillary and the inlet vial buffer solutions contain the tRNA and/or any other components to be transfected. Cells are placed in a chamber on the microscope stage, and cell bathing medium (HEPES buffer) is electrically grounded. The capillary outlet is placed within 5 µm of the cell surface, and the DC high voltage power supply is connected.

In another, non-limiting exemplary electroporation protocol, cells are electroporated using a modified patch-clamp technique. Single cells under direct observation are indented with a microelectrode and electroporated using a current delivered from a simple voltage-clamp circuit, as described in detail in Rae J L and Levis R A, Single-cell electroporation, Pflugers Arch 443 (4):664-70, 2002.

In another, non-limiting exemplary electroporation protocol successfully used for electroporation of DNA, but equally useful for tRNA, into individual neurons in cultures of organotypic brain slices (FIG. 4), micropipettes with a tip diameter of about 1-2 µm and with resistances of 10-20 MΩ are pulled from capillary glass with filament (available from Science Products, Hofheim, Germany, catalogue number GB 150F-8P) on a Micropipette Puller (available from Sutter Instrument Company, Novato, USA catalogue number P-97). Micropipettes are mounted on a three-axis micromanipulator (Luigs and Neumann, Ratingen, Germany). A Millicell CM insert (Millipore, Billerica, Mass., USA) containing a brain slice is placed in a perfusion chamber on the stage of a Zeiss Axioplan™ microscope and continuously perfused with oxygenated physiological salt solution during electroporation. The overall time under perfusion is typically about 30 min. Slices are transferred back into the incubator, individual cell somata are identified, and a pipette tip is gently placed against the cell membrane. Voltage pulses are delivered between an electrode placed inside the micropipette in contact with the tRNA solution (cathode), and a ground electrode (anode) using an isolated voltage stimulator (available from WPI, Berlin, Germany, under the name HI-MED HG-203) controlled by a tetanizer (available from Sigmann Elektronik, Hueffenbart, Germany). To prevent the tip from clogging and dilution of the tRNA, a back-pressure (typically 2-10 mbar) is applied to the pipette. In an exemplary embodiment, a single train of 200 square pulses with a duration of 1 ms is applied, using a 4 ms delay with an amplitude of 10 V. The 1 ms pulses remove the negatively charged tRNA from the pipette by electrophoresis, driving electroporation. Typically, no voltage is applied during the delay of 4 ms between the pulses and thus there is no current flowing through the circuit.

Each method for introduction of tRNA or nucleic acid into a cell represents a separate embodiment of the present invention.

Introduction of Nucleic Acid Molecules into Subcellular Compartments

Vestweber and Schatz (Nature 338: 170-172, 1989) achieved uptake of both single- and double-stranded oligonucleotides into yeast mitochondria by coupling the 5' end of the oligonucleotide to a precursor protein consisting of the yeast cytochrome c oxidase subunit. Seibel et al. (Nucleic Acids Research 23: 10-17, 1995) reported the import into the mitochondrial matrix of double-stranded DNA molecules conjugated to the amino-terminal leader peptide of the rat ornithine-transcarbamylase.

Methods for the introduction of nucleic acid molecules into the interior of an organelle are disclosed in WO2003/052067. WO2005/001062 discloses the use of viral vectors that contain localization signals specific for the target organelle. These protocols can be utilized for the introduction of labeled tRNAs or some other part of the ribosome into the mitochondria or chloroplast.

Labeling and Detection According to the Present Invention

In other embodiments, methods of the invention can be carried out in accordance with the following alternatives:

Ribosomal Labeling.

In this embodiment the donor and/or acceptor fluorophore or fluorophores are attached to the ribosome large subunit and/or small subunit by using fluorescent oligonucleotide DNA probes (FIG. 2) as discussed in detail in Amann et al., Microbiological Reviews, 59:143-169, 1995; Fuchs et al, Appl Environ Microbiol 67: 961-968, 2001; Behrens et al, Appl Environ Microbiol 69:4935-4941, 2003), which are incorporated herein by reference.

According to one embodiment, a FRET pair of fluorescent oligonucleotide DNA probes is used to estimate the abundance of assembled ribosomes. According to another embodiment a quench pair of ribosome large subunit and/or small subunit is used to estimate the abundance of disassembled ribosomes. According to another embodiment, the ratio of assembled ribosomes is detected by the measurement of both said FRET and quench pairs. "Quenching pair" and "quench pair" as used herein refer to a fluorophore in combination with a second molecule that quenches fluorescence of the fluorophore when in close proximity thereto. Thus, when the quenching pair is separated, under conditions wherein the fluorophore emits radiation, a detectable signal can be emitted.

Probe pairs that can attach to accessible parts of the assembled ribosome and have a distance compatible with the requirements of FRET are presented in Table 1 (TT denotes *Thermus Thermofilus*, EC denotes *E. Coli*).

TABLE 1

Oligonucleotide probe pairs

| Large (23S) subunit Oligo probe | | | Small (16S) subunit Oligo probe | | | |
|---|---|---|---|---|---|---|
| Sequence | TT position | EC position | Sequence | TT position | EC position | Distance range (Å) |
| TATCAGCGTG CCTTCTCC (SEQ ID NO: 1) | 1744-1759 | 1696-1713 | AAAGTGGTAA GCGCCCTC (SEQ ID NO: 6) | 1436-1450 | 1455-1472 | 11-60 |
| TATCAGCGTG CCTTCTCC (SEQ ID NO: 1) | 1744-1759 | 1696-1713 | ACCCCAGTCA TGAATCAC (SEQ ID NO: 7) | 1451-1468 | 1473-1490 | 10-40 |
| TATCAGCGTG CCTTCTCC (SEQ ID NO: 1) | 1744-1759 | 1696-1713 | AGCCGTTACC CCACCTA (SEQ ID NO: 8) | 248-264 | 252-268 | 20-60 |
| TATCAGCGTG CCTTCTCC (SEQ ID NO: 1) | 1744-1759 | 1696-1713 | GCTGCCTCCC GTAGGAGT (SEQ ID NO: 9) | 334-351 | 338-355 | 30-70 |
| CGACGTTYTA AACCCAGCTC (SEQ ID NO: 5) | 2589-2608 | 2576-2595 | AAGCTACCTA CTTCTTTT (SEQ ID NO: 10) | 1411-1426 | 1428-1445 | 25-70 |

Labeling for Estimation of Ribosomal Subunit Assembly.

According to another embodiment, the large and small ribosomal subunits are labeled with a FRET pair, wherein the obtained signal is proportional to the abundance of assembled ribosomes. According to another embodiment, the large and small ribosomal subunits are labeled with a donor/quencher pair, wherein the obtained signal is proportional to the abundance of dissociated ribosomes. According to a further embodiment, the ribosome subunits are labeled with both a FRET pair and a donor/quencher pair, wherein the ratio of assembled to dissociated ribosomes is estimated.

A list of ribosomal protein pairs suitable to be used as a FRET pair or as a donor/quencher pair is provided in Table 2. The data is compiled from the *Thermus Thermophilus* structure and therefore is relevant for most prokaryotes.

TABLE 2

Ribosomal protein pairs

| 50S Ribosomal protein | 30S ribosomal protein | Distance range (Å) |
|---|---|---|
| L5 | S13 | 12-90 |
| L1 | S11 | 40-110 |
| L2 | S6 | 6-60 |
| L19 | S20 | 30-70 |
| L14 | S12 | 15-90 |

Ribosomal Protein Labeling.

In this embodiment the donor and/or acceptor fluorophore or fluorophores are attached to the ribosomal proteins by fusing the protein of choice with a naturally fluorescent protein, such as green fluorescent protein, yellow/cyan/blue fluorescent proteins or any other naturally fluorescent protein. An example wherein L1 was labeled by fusion with a naturally fluorescent protein is described in Mascarenhas et al (EMBO Rep. 2 (8): 685-689, 2001), incorporated herein by reference.

Organic dyes can be used to label ribosomal proteins using standard protein labeling techniques. Suppliers of these dyes publish detailed protocols describing their use. General procedures label proteins through their amino groups (lysine). Other procedures target cysteines which are sometimes available for precisely located labeling. In this way, ribosomal proteins S1 and S8 were labeled by coumarin (Bakin et al, 1991, J Mol Biol. 221 (2): 441-453), and ribosomal proteins were tagged with fluorescein attached to a cysteine residue (Odom et al., 1990, Biochemistry, 10734-10744).

tRNA Labeling.

In this embodiment the donor and/or acceptor fluorophore or fluorophores are attached to one or more species of tRNAs, or even total bulk tRNA that includes all tRNA moieties. Methods for fluorophore labeling of tRNA are well known in the art and are described inter alia in U.S. Pat. No. 7,288,372 and U.S. Patent applications 2003/0219780 and 2003/0092031, which are incorporated herein by reference.

In another exemplary method, used for Met-tRNA (Jun S Y et al, Fluorescent labeling of cell-free synthesized proteins with fluorophore-conjugated methionylated tRNA derived from in vitro transcribed tRNA. J Microbiol Methods. 2008 June; 73 (3):247-51) but suitable for any tRNA, 10 μl of 30 mM succinimidyl ester of fluorescent dye in dimethyl sulfoxide (DMSO) is added to 40 μl of the Met-tRNA-fMet-resuspended solution and incubated for 40 min on ice. The reaction is stopped by adding one-tenth volume of 2M sodium acetate, pH 5.0. Fluorophore-conjugated Met-tRNA-fMet is extracted repeatedly with an equal volume of acid phenol: chloroform (1:1, v/v; pH 5.0. Two and a half volumes of cold 95% (v/v) ethanol solution are added to the aqueous phase, and the mixture is allowed to stand at −70° C. for 1 h to precipitate fluorophore-conjugated Met-tRNA-fMet. The precipitated pellet is collected by micro-centrifugation at 14,000 rpm at 4° C. for 20 min, and then resuspended in an equal volume of diethyl pyrocarbonate (DEPC)-treated water to the original reaction volume. After alcohol precipitation, the precipitate is washed with 80% (v/v) ethanol solution, dried under vacuum, and resuspended in 20 µl of DEPC-treated water.

In another exemplary method, used for conjugation of BODIPY-FL to Met-tRNA (Olejnik J et al, N-terminal labeling of proteins using initiator tRNA. Methods. 2005 July; 36 (3):252-60), but suitable for conjugation of BODIPY-FL to any tRNA, 1.0 $OD_{260}$ (1500 pmol) of methionyl-tRNA-fMet (tRNA-fMet [Sigma Chemicals, St. Louis, Mo.], aminoacylated with methionine) is dissolved in water (37.5 µl), followed by addition of 2.5 µl of 1N $NaHCO_3$ (final conc. 50 mM, pH 8.5), followed by 10 µl of 10 mM BODIPYFL-SSE solution (Molecular Probes, Eugene, Oreg.). The modification reaction is allowed to proceed for 10 min at 0° C. and quenched by the addition of 0.1 volume of 1M lysine. 0.1 volume of 3M NaOAc, pH 5.0, is added, and modified tRNA is precipitated with 3 volumes of ethanol, dissolved in 50 µl of water, and purified on a NAP-5 column (Amersham-Pharmacia, Piscataway, N.J.) to remove any free fluorescent reagent.

In general, tRNA molecules can be tagged while retaining their interaction with the aminoacyl synthetases as well as retaining their functionality with the ribosome. tRNAs have been tagged with fluorescein (Watson et al., 1995, Biochemistry. 34 (24): 7904-12), with tetra methyl rhodamine (TMR) (Jia et al., 1997, Proc Natl Acad Sci USA. 7932-6), and with proflavine and ethidium bromide.

Certain preferred embodiments of the present invention include labeling the tRNA with small organic dyes attached to the "shoulder" region of the tRNA, such as in positions 8 and 47 of E. Coli tRNAs, which have been often used for this purpose. One particular labeling method is attaching the label of choice to one or both of the dihydrouridines in the D-Loop of the tRNA. Most tRNA have these dihydrouridine modifications, enabling a wide choice of labels, including rhodamines, which are very useful due to their low tendency to bleach and high signal strength. The most widely used dyes are FITC and TMR (excitation peaks at 550 nm and emission at 573 nm).

In another embodiment of the present invention, a specific tRNA species or bulk tRNA (non-specific) is labeled with the donor fluorescent label. Other specific or non-specific tRNA are labeled with the acceptor fluorescent label. The labeled tRNA mixture is administered to the cells. FRET will occur only when neighboring sites in the ribosome (for example A and P, or P and E) are occupied by a donor-acceptor pair. For example, if 10% of all cellular tRNA is labeled, then on average approximately 1% of active ribosomes will be in a FRET configuration (0.25% in each of PA, AP, PE, EP configurations, where A, P, E indicate the ribosomal tRNA sites, and donor is assumed always to be in the first and acceptor in the second site).

According to another embodiment of the present invention, the ratio of immobilized tRNAs in adjacent ribosomal sites is detected by measurement of FRET resulting from interaction between the tRNAs with donor and acceptor fluorophores. When both the donor and the acceptor fluorophores are attached to one or more species of the tRNAs, an elongation activity is detected.

According to another embodiment of the present invention, the ratio of immobilized tRNAs is detected by the measurement of tRNAs with single fluorophores, which produce the isotropic signal detected by anisotropy microscopy only when immobilized.

Amino Acid Labeling.

Methods of fluorescent labeling of amino acids are well known in the art and are disclosed in WO2004/050825, which is incorporated herein by reference. Fluorescent moieties useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids. Upon excitation at a pre-selected wavelength, the marker is detectable at low concentrations either visually or using conventional fluorescence detection methods. According to the present invention, while both the donor and the acceptor fluorophores are attached to one or more amino acids, an elongation activity is detected.

Translation Factor Labeling.

In another embodiment, the translation factor of the present invention is selected from the group consisting of a preinitiation factor, an initiation factor, an elongation factor, a termination factor, a recycling factor, an amino-acyl synthetase and a peptidyl transferase.

In another embodiment, two components of the preinitiation or initiation complex are identified and labeled with donor and/or acceptor fluorophore or fluorophores. The detected FRET signal is proportional to abundance of assembled complexes.

Labeling Strategies for Initiation Factors.

In prokaryotes, the process of translation initiation is well documented (Laursen et al., 2005, Microbiol Mol Biol Rev. 69 (1):101-123). Briefly, binding of IF3 to the 30S ribosomal subunit promotes dissociation of the ribosome into subunits and thus couples ribosome recycling and translation initiation. Initiation factor IF1 binds specifically to the base of the A-site of the 30S ribosomal subunit and is thought to direct the initiator tRNA to the ribosomal P-site by blocking the A-site. Following subunit dissociation, IF2, mRNA, and fMet-tRNA associate with the 30S ribosomal subunit. The three factors bind to the ribosome, and are brought together transiently. Thus, identification of immobilization of one of the three factors, or formation of a FRET pair, identifies an ongoing process of translation. This is in contrast with other assay strategies, for example immobilization of tRNA in a ribosome, which means that the A, P or E site is occupied, but does not necessarily mean that translation is in progress, as some antibiotics are known to "freeze" the ribosome with tRNA in place.

With this strategy, as with other strategies known in the art, including, but not limited to FCS, measurement of signal variability provides an estimate of the number of initiation events.

Several strategies are possible for monitoring factor immobilization or co-binding. According to one embodiment, any one of the factors can be labeled and anisotropy microscopy is used to identify the binding event. In this embodiment, IF1 is a prime candidate due to its small size (about 8 KDa). According to another embodiment, another pair of components of the translation machinery is labeled as FRET pair, with the emission of a FRET signal indicative of the transient state of the machinery.

Apparatuses for Study of Translation in Subcellular Compartments and Uses Thereof.

Methods of the present invention enable monitoring of translation in various specific subcellular compartments such as mitochondria, chloroplasts, and dendritic spines. In mitochondria and chloroplasts, the entire translation apparatus, including ribosomes, ribosomal proteins, translation factors, tRNAs and the genetic code, are specific to the subcellular compartment and distinct from those of the host eukaryotic cell. Also, apart from the ribosomal RNA and tRNA, other proteins of the translation apparatus are synthesized in the cell cytoplasm and imported into the subcellular compartment. This allows a specific assay to be developed, wherein the proteins of choice are labeled in the cell, either by techniques of genetic engineering or by introducing the labeled proteins into the cells. In both cases, the labeled proteins are directed to and imported into the subcellular compartment. Thus the measured signals pertain to subcellular compartment only and not to the general cellular translation apparatus. This type of assay can be useful, for example, in the study of adverse effects of antibiotics, which are mainly to be expected in mitochondria due to the large similarity between mitochondrial ribosomes and those of microorganisms.

Host Cells

Any cell is suitable for assaying translation by methods of the present invention. Non-limiting examples of target cell types are COS, HEK-293, BHK, CHO, TM4, CVI, VERO-76, HELA, MDCK, BRL 3A, NIH/3T3 cells, etc. Additional cell lines are well known to those of ordinary skill in the art, and a wide variety of suitable cell lines are available from the American Type Culture Collection, 10801 University Boulevard, Manassas, Va. 20110-2209. Cells of particular interest include neuronal cells, immune system cells, including lymphocytes (B and T cells e.g., T helper cells) and leucocytes (e.g., granulocytes, lymphocytes, macrophage and monocytes), cells from lymph, spleen and bone marrow tissues, epithelial cells, and cells from or derived from internal organs.

Signal Detection

The signals emitted by the cells or organelles as disclosed in the present invention can be detected by several different instrument configurations. As a bulk assay, it can potentially be read manually, by comparing the fluorescent signal to calibrated standards under a fluorescent reader. Alternatively, it can be read by a fluorescent plate reader, made for 96 well plates, 384 well plates, or any other configuration. In another embodiment, the labeled cells are imaged by a microscope, to identify subcellular localization of protein synthesis processes and to estimate the relative rates of protein synthesis in various regions of the cell. In further embodiments, instruments capable of single-molecule detection in live cells are used.

Signal Analysis

There are numerous methods to process and analyze the resulting signals. In one embodiment, donor, acceptor and FRET signals are separately measured and compared to yield the fraction of pairs in FRET position versus the total concentration of donors and acceptors separately. When repeating such measurements with various concentrations of labeled components vs. the unlabeled, it is easy to derive the overall fraction of component pairs versus the total number of components. For example, if 10% of tRNA are labeled as donors and 10% as acceptors, then about 4% of active ribosomes will include a FRET tRNA pair in neighboring ribosomal positions (1% AP, 1% PA, 1% PE, 1% EP, where donor is always first and acceptor second). This creates a specific ratio of donor/acceptor/FRET signals. If only 5% are labeled as donors or acceptors, than only 1% FRET signal will occur. Thus the FRET signal strength is proportional to the square of the donor/acceptor signals. This allows a calibration curve to be derived, for example in cell-free system, and later used in live cells to provide a precise estimate of the relative concentration of components in FRET position as well as the concentration of all components. This analysis is identical in the case that the labels are applied to ribosomal subunits, to ribosome and initiation factor, or any other combination of two components of the protein translation system.

In another embodiment, signal variance is computed, and the square of the ratio of average signal to average variance is computed, which yields an estimation of the number of labeled components being measured. This assumes that the process underlying this variation is of Poissonian or Gaussian nature, such as in molecules diffusing into and out of a certain volume, or the blinking of labeled ribosomes in response to protein synthesis. When considering a sizable number of ribosomes (10 or more), the process can be assumed to be governed by Poissonian or Gaussian statistics, depending on the number. In such cases, as is well known, the variability of the signal is proportional to the square root of the signal strength. For example, let the measured signal be denoted by $S_t$, and let its average over a period of time (for example a few seconds) be denoted by $S_{av}$. The variance $Var(S)=average(S_t-S_{av})$. In such processes, the size of the variance is on average the square root of the signal. Thus $Var(S) \sim sqrt(S_{av})=sqrt(NS)$ where S is the signal from a single event (for example FRET from a pair of labeled components). This means that $(S/Var(S))^2 = NS/S = N$ or the number of active particles.

Fluorescence Anisotropy

Fluorescence anisotropy is based on the principle of photoselective excitation of fluorophores by polarized light. In an isotropic solution, the fluorophores are oriented randomly. Excitation with polarized light results in a selective excitation of those fluorophore molecules whose absorption transition dipole is parallel to the electric vector of the excitation. This selective excitation results in a partially oriented population of polarized fluorescence emission. If the excited fluorophores are immobile, emission occurs with the light polarized along the same axis in which excitation occurred.

However, for a molecule that undergoes rotational diffusion during the lifetime of the excited state, the emission will take place in a basically random direction, and polarization will be relatively random (this depends on the relationship between the lifetime of the fluorophore and the rate of rotation).

Conveniently, rotation correlation times for macromolecules are on the order of nanoseconds. For example, the rotational correlation time for human serum albumen is around 50 ns. When a molecule (such as a fluorescent labeled tRNA) binds to a large complex such as the ribosome, it will have a longer rotational correlation time. This can be observed as a change in the anisotropy of the complex with respect to the unbound molecule.

Application of the Present Invention for Diagnostic Applications

The methods disclosed herein are suitable for diagnostic applications, wherein rates of protein synthesis are indicative of type or phase of a disease or condition. For the purpose of diagnosis, cells are obtained from the host, for example, from biopsy, and prepared for the assay. In another embodiment, the preparation comprises the following steps:
  (a) introducing the labeled translation system components into the by means of transfection; and
  (b) detecting radiation emitted from the cells.

In another embodiment, the method further comprises the step of analyzing the radiation or a signal derived thereof, thereby obtaining a readout of translation activity.

Prior to detection, cells are commonly transferred to a carrier. The type of carrier depends on the type of measurement that is used for detection. Thus, a carrier includes, but is not limited to, a fluorescent plate reader.

In another embodiment, the above method is applied in a high-throughput operation. In another embodiment, the method is applicable for accurate measurements of subcellular localization of protein synthesis events, for example, detection of translation activity in mitochondria or neuronal spines.

Application of the Present Invention for High Throughput Screening (HTS) Assays

The methods disclosed herein can optionally be used for the screening of a large library of small molecules, recombinant proteins, peptides, antibodies, or other compounds to determine their efficacy or their potential for use as drugs, based on measuring the effect of a test compound on general translation in a test cell. High-throughput screening typically utilizes an assay that is compatible with the screening instrument, enables quick rejection of most of the compounds as irrelevant, and approves only a small fraction for continued research. The present invention is suitable for a very thorough and informative assay, as explained above, in the sense that it provides real-time measurement of general ribosomal activity in viable cells.

Thus, functional activity of a compound on a specific cell type can be usefully studied by subjecting it to translation monitoring assay as disclosed herein. A cell line with tagged elements is cultured and placed in a multi well plate. This can have a 96 well plate format, a 384 well plate format or any other format compatible with automated screening. The wells in the plate need to be optically amenable for detection.

A robot administers one compound from the library into each well, and signal detection is performed. A suitable sampling regime should be adopted. As an illustrative example a protein translation monitoring measurement for 30 seconds every 10 minutes for a total of one hour. Other regimes can optionally be also used. The effect of the compound on translation activity can thus be detected.

It is understood by the skilled artisan that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additional washing steps, blocking steps, etc. It is understood that the exemplary embodiments provided herein in no way serve to limit the true scope of this invention, but rather are presented for illustrative purposes. All references cited herein are expressly incorporated by reference in their entirety.

Determination of Minimum Inhibitory Concentration (MIC)

According to some embodiments of the present invention, the test cells are bacterial cells. As a secondary assay, the minimum inhibitory concentration (MIC) against bacterial organisms is determined for each test compound that is positive in the translation-screening assay. Methods known in the art may be used such as broth micro-dilution testing, using a range of concentrations of each test compound (1993, National Committee for Clinical Laboratory Standards, Methods for Dilution Anti-microbial Susceptibility Tests For Bacteria That Grow Aerobically-Third Edition: Approved Standard, M7-A3). The MIC against a variety of pathogens are determined using the same method. Pathogenic species to be tested generally include: *E. coli, Enterococcus faecium, Enterococcus faecalis, Streptococcus pneumoniae, Staphylococcus aureus, Klebsiella pneumoniae, Pseudomonas aeruginosa, Staphylococcus epidermis, Shigella flexneri*, and *Salmonella typhimurium*.

During the evaluation of positive compounds of this embodiment and selection of leads for further development, the two main considerations will be antibacterial activity and chemical structure. To be considered for further development, a compound should inhibit preferably the growth of both Gram positive and Gram negative bacteria. The chemical structure should preferably be amenable to further chemical modification, so that analogs and derivatives can be synthesized and analyzed for structure-activity relationship and other preclinical studies, such as toxicology, pharmacokinetics, and drug metabolism.

Definitions

The term "translation activity" as used herein refers to any step during the transition from mRNA to an amino acid sequence, including, but not limited to, assembly of the initiation or pre-initiation complex, attachment of an mRNA to a ribosomal subunit, assembly of the entire ribosome particle, mRNA-tRNA recognition and pairing (also known as "codon-anti codon paring"), amino acid activation (i.e. adenylation of the amino acid to produce aminoacyl-AMP), tRNA aminoacylation (i.e. attachment of an amino acid to the tRNA), attachment of the recycling factor, and addition of the amino acid to a growing polypeptide chain. Each possibility represents a separate embodiment of the present invention.

The term "translation factor" refers to any one or more factors involved in protein translation, including, but not limited to, preinitiation factor, initiation factor, elongation factor, termination factor, recycling factor, amino-acyl synthetase and peptidyl transferase.

The term "mRNA" is used herein to describe a ribonucleotide sequence that transfers genetic information to ribosomes, where it serves as a template for protein synthesis. Ribonucleotide sequences are polymers of ribonucleic acids, and are constituents of all living cells and many viruses. They consist of a long, usually single-stranded chain of alternating phosphate and ribose units with the bases adenine, guanine, cytosine, and uracil bonded to the ribose. The structure and base sequence of RNA are determinants of protein synthesis and the transmission of genetic information.

As used herein, the term "tRNA" refers to transfer ribonucleic acid. An "initiator tRNA" is a specific tRNA molecule that is used only for the initial amino acid of a synthesized polypeptide. A "suppressor tRNA" is a tRNA molecule that comprises an anticodon which allows pairing with a termination codon (e.g. UAG and UAA). An "elongator tRNA" is a tRNA molecule that is neither an initiator nor a suppressor, and that places its corresponding amino acid or codon in its proper sequence during the process of translation.

As used herein, "cell" refers to a prokaryotic or a eukaryotic cell. Suitable cells can be, for example, of mammalian, avian, insect, bacterial, yeast or plant origin. Non-limiting examples of mammalian cells include human, bovine, ovine, porcine, murine, and rabbit cells. In another embodiment, the cell can be an embryonic cell, bone marrow stem cell, or other progenitor cell. In another embodiment, the cell is a somatic cell, which can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The term "test cell" as used herein, refers to cells that are manipulated for use in the translation assay of the invention.

The term "host cell" as used herein refers to cells that do not naturally contain the labeled protein synthesis elements of the invention.

In another embodiment, the biological sample of the present invention is a subcellular compartment. As used herein, the term "subcellular compartment" refers to any defined part of the cell where protein translation activity takes place, such as dendritic spines, mitochondria, endoplasmic reticulum (ER) and chloroplasts.

In another embodiment, the biological sample of the present invention is an organelle. As used herein, the term "organelle" refers to cellular membrane-encapsulated structures such as the chloroplast, endoplasmic reticulum (ER) and mitochondrion.

As used herein, "introducing" refers to the transfer of molecules such as ribosomes, tRNAs, translation factors and amino acids from outside a host cell or subcellular compartment to inside a host cell or subcellular compartment. Said molecules can be "introduced" into a host cell or subcellular compartment by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a host cell or subcellular compartment include, but are not limited to heat shock, calcium phosphate transfection, electroporation, lipofection, and viral-mediated transfer.

As used herein, the term "transfection" refers to introduction of a nucleic acid sequence into the interior of a membrane-enclosed space of a living cell, including introduction of the nucleic acid sequence into the cytosol of a cell as well as the interior space of a mitochondria, endoplasmic reticulum (ER) or chloroplast. The nucleic acid may be in the form of naked DNA, RNA, or tRNA. The DNA, RNA, or tRNA is in some embodiments associated with one or more proteins. In another embodiment, the nucleic acid is incorporated into a vector. Each possibility represents a separate embodiment of the present invention.

As used herein, the term "infection" means the introduction of a nucleic acid such as DNA, RNA, tRNA into a recipient cell, subcellular compartment, or organism, by means of a virus. Viral infection of a host cell is a technique that is well established in the art and is described in a number of laboratory texts and manuals such as Sambrook et al., Molecular Cloning: A Laboratory Manual, Vol. 1-3, Cold Spring Harbor Laboratory, Cold Spring Harbor, N.Y., 2001.

As used herein, the term "label" or "detectable label" means a molecule that can be directly (i.e., a primary label) or indirectly (i.e., a secondary label) detected. For example, a label can be visualized and/or measured and/or otherwise identified so that its presence, absence, or a parameter or characteristic thereof can be measured and/or determined.

As used herein, the term "fluorescent label" refers to any molecule that can be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, Malachite green, stilbene, Lucifer Yellow, Cascade BluerM, Texas Red, IAEDANS, EDANS, BODIPY FL, LC Red 640, Cy 3, Cy 5, Cy 5.5, Alexa, LC Red 705 and Oregon green, as well as to fluorescent derivatives thereof. Suitable optical dyes are described in The Tenth Edition of Haugland, R P. The Handbook: A Guide to Fluorescent Probes and Labeling Technologies. 10th. Invitrogen/Molecular Probes; Carlsbad, Calif.: 2005, hereby expressly incorporated by reference. Additional labels include but are not limit to fluorescent proteins, such as green fluorescent protein (GFP), yellow fluorescent protein (YFP), blue fluorescent protein (BFP), cyan fluorescent protein (CFP) etc.

As used herein, "tags" can refer to any label known in the art, which can be detected either directly or indirectly.

As used herein, the term "test compound" refers to a compound to be tested by one or more screening assays of the invention as a putative agent that modulates translation activity. The test compounds of the invention encompass numerous classes of chemical molecules, though typically they are organic molecules, and preferentially of low molecular weight.

The term "modulator" as used herein is generic for an inhibitor or activator of translation.

EXAMPLES

Example 1

Labeling Two Parts of the Translational Machinery as a FRET Pair

Two parts of the translational machinery are labeled as a FRET pair. For example, some tRNAs (FIG. 1) can be labeled with a donor fluorophore, and others with a corresponding acceptor fluorophore. An example of such a pair is FITC (excitation and emission peaks are 494 and 520 nm, respectively) and TMR (excitation and emission peaks at 550 and 573 nm, respectively); when translation is active, such tRNAs are immobilized in two adjacent sites (A and P or P and E) of the ribosome, thereby producing a FRET pair which produces measurable FRET signals. These signals indicate that the A and P sites are populated with labeled tRNAs. A small signal indicates that a low percentage of the A and P sites are populated, and therefore that the translation apparatus is in a state of low production rates. Additional exemplary, non-limiting FRET combinations are listed in Table 3.

TABLE 3

Exemplary FRET combinations.

| Donor fluorophore | Acceptor fluorophore |
|---|---|
| GFP | TMR |
| BFP | FITC |
| FlAsH (Fluorescein Arsenical Helix binder; 4',5'-bis(1,3,2-dithioarsolan-2-yl)fluorescein) | TMR |
| Qdot ™ 525 | TMR |
| Cy3 | Cy5 |

Three docked tRNAs are shown in FIG. 1. The first 32 is in the A (Aminoacyl) site; the second (33) in the P (Peptidyl) site, and the amino acid it carries is at this point connected to the nascent peptide; the third (34) is in the E (exit) site, it has been discharged from the amino acid and will be ejected shortly from the ribosome. The heavy line 30 indicates the mRNA being translated, and the dotted line 45 represents the polypeptide being synthesized, tied into the Peptidyl position.

The main stages of elongation are as follows. Stage 1: Codon recognition. A tRNA molecule carrying an amino acid binds to a vacant A-site, while the nascent polypeptide is attached to the P-site. Stage 2: Peptide bond creation. A new peptide bond is created and the polypeptide chain is moved to the A-site. Stage 3: Translocation. The ribosome translocates a distance of 3 nucleotides with respect to the mRNA, the two tRNA units and the polypeptide chain. Stage 4: the cycle repeats itself until a stop codon is reached.

Three types of tRNA are shown with respect to fluorescent labeling. The tRNAs 40 and 43 are unlabeled. tRNAs 33, 34 and 42 (marked with vertical lines) are labeled as FRET donors. tRNAs 41 and 32 (marked with horizontal lines) are labeled as FRET acceptors. When freely diffusing (as in the case of 41 and 42), the chance of a FRET pair forming for a measurable length of time is negligible. However, when a pair is immobilized on the ribosome (as in the case of 32 and 33), a FRET pair is formed for about 50 milliseconds, which is sufficient for detection.

The more active the translation system, the larger the probability of juxtaposition of such pairs, and the larger the FRET signal. In addition, signal variability can be used to estimate the concentration of active ribosomes. Also, with a microscope, subcellular localization of protein synthesis can be quantitatively estimated. tRNAs pairs that are not immobilized in such a way either diffuse in the cytoplasm or else are bound to non-labeled molecules such as translation factors or amino-acyl synthetases, and therefore do not create FRET pairs, yielding no measurable signal. This basic principle holds for any choice of FRET pairs.

Numerous pairs of the translational machinery can be considered for such assays, yielding particular pieces of information. Some of these are shown in Table 4 and Table 5.

TABLE 4

FRET pairs

| Donor | Acceptor | Translation stage measured |
| --- | --- | --- |
| Initiation factor | Initiation factor | Initiation |
| Initiation factor | Ribosomal protein | Initiation |
| tRNA | tRNA | Elongation |
| Amino acids | tRNA | Elongation |
| Amino acids | Amino acids | Elongation |
| Termination factor | tRNA | Termination |
| Recycling factor | Ribosome | Recycling |

When tRNAs are labeled, one or more specific moieties may be labeled, or bulk tRNA of all species may be labeled as well.

TABLE 5

Labeling Strategy Variants

| Measured property | Measurement Technique | Comments |
| --- | --- | --- |
| Ratio of assembled ribosomes | FRET between fluorescent OligoDNA probes (FIG. 2) | Signal is created by FRET pair on small/large ribosomal subunits |
| Ratio of assembled ribosomes | FRET between labeled ribosomal proteins | Ribosomal proteins are fused to fluorescent proteins or attached to fluorescent dyes |
| Ratio of immobilized tRNA | FRET between tRNA pair in A and P sites | tRNA with donor and acceptor fluorophores are introduced, only those immobilized in adjacent ribosomal sites produce FRET |
| Ratio of initializing ribosomes | FRET between initiation factor and other initiation factor or ribosomal protein | Donor on initiation factor, acceptor on another initiation factor or on ribosomal protein or rRNA |

Example 2

Labeling One Part of the Translational Machinery with a Single Fluorophore

The single fluorophore method makes use of the technique of fluorescent anisotropy microscopy (see above). Thus, tRNAs which are freely diffusing in the cytoplasm produce a fluorescent signal that is only weakly polarized (in the polarization oriented as the excitation radiation), but tRNAs which are bound to ribosomes (which are thousands of times more massive) yield a highly polarized fluorescent signal, where the polarization is in the same plane as the excitation radiation.

According to this embodiment, only one part of the translational machinery is labeled. The total signal is related to the fraction of bound labeled molecules. The more active the translation system, the larger the probability of production of such bound molecules and the larger the signal. Numerous members of the translation machinery can be considered for such assays, yielding particular pieces of information. Some of these are shown in Table 6.

TABLE 6

Labeling with a single Fluorophore

| Labeled molecule | Translation stage measured |
| --- | --- |
| Initiation factor | Initiation |
| tRNA | Elongation |
| Amino acids | Elongation |
| Termination factor | Termination |

Example 3

Introduction of the Labeled tRNAs into CHO Cells

Labeled tRNAs are transfected into CHO cells using Trans-Messenger transfection reagent (Qiagen, Hilden, Germany) according to the manufacturer's protocol. Transfected cells are placed under a microscope equipped for single molecule detection (Zeiss, Oberkochen, Germany) with an image acquisition device operable at a sufficient rate (10-100 frames per second), and computational units that can acquire and analyze the resulting images and data (FIG. 3). General ribosomal activity is measured.

For high-throughput screening, transfected cells are cultured in a 96-well plate format, compatible with automated screening. A robot administers one compound out of the library being screened into each well and translation detection is performed. A suitable sampling regime is adopted. The effect of the compound on translation activity is detected in comparison with negative control signal.

Example 4

Diagnostic Applications

Bulk yeast tRNA is labeled with donor fluorophore and stored. Another batch of bulk yeast tRNA is labeled with acceptor fluorophore and stored. Prior to the assay, two aliquots of donor- and acceptor-labeled tRNA are mixed. The mixture is transfected into the cells to be diagnosed, for example, by using the transfection kit INTERFERin™ (Autogen Bioclear™, Wiltshire, UK). The cells may be human cells, for example, human cells obtained from a tissue removed by biopsy. The transfected cells are introduced into a 96 well-plate. Signals are collected from the plates using a fluorescent plate reader and are subjected to computerized analysis/es. Typically, the parameters derived for the analysis are: average signal strength, average signal deviation, or concentration of active ribosomes in each well. These parameters are monitored over time and in response to treatment. Values before and/or after treatment are compared to known standards to infer clinical parameters of the cells.

It should be understood that the detailed description and specific examples, while indicating preferred embodiments of the invention, are given by way of illustration only, since various changes and modifications within the spirit and scope of the invention will become apparent to those skilled in the art from this detailed description.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for measuring translation activity, which comprises:
   labeling at least one tRNA with a first label and at least one tRNA with a second label, wherein when the first label and the second label are in proximity a detectable electromagnetic radiation is produced;
   introducing into a biological sample the at least one tRNA labeled with the first label and the at least one tRNA labeled with the second label, wherein said labels produce electromagnetic radiation in response to overall protein translation activity in said biological sample, wherein said biological sample is an intact cell;
   detecting said electromagnetic radiation from the sample;
   analyzing said electromagnetic radiation to produce a readout of a parameter of translation activity, wherein the parameter is selected from the group consisting of rate of translational activity, ratio of labeled versus unlabeled tRNA, location of translation activity, and average translation speed; and
   comparing said readout to a reference standard thereby determining an estimate of overall translation activity in real time without identifying a protein synthesized.

2. The method of claim 1, which further comprises irradiating the biological sample with a source of electromagnetic radiation prior to the step of detecting said electromagnetic radiation.

3. The method of claim 1, which further comprises administering to the intact cell a drug candidate prior to detecting the electromagnetic radiation.

4. The method of claim 3, which further comprises
   performing the labeling, introducing, detecting, analyzing and comparing on separate biological samples which samples are identical, except that one of the separate biological samples has not been contacted with the drug candidate, wherein said detecting provides a quantity of electromagnetic radiation of the biological sample contacted with the drug candidate and a quantity of electromagnetic radiation of the biological sample not contacted with the drug candidate; and comparing the quantity of electromagnetic radiation of the biological sample contacted with drug candidate with the quantity of electromagnetic radiation of the biological sample not contacted with the drug candidate, with a difference between these two quantities indicating that the drug candidate affects said overall protein translation.

5. The method of claim 4, wherein the drug candidate is selected from the group consisting of a small molecule, a peptide, an enzyme, a hormone, a biotherapeutic agent, and an antibiotic.

6. The method of claim 1, wherein said first label and second label together form a Fluorescence Resonance Energy Transfer (FRET) pair comprising donor-acceptor fluorophores.

7. The method of claim 6, wherein the FRET pair is selected from the group consisting of GFP-TMR, BFP-FITC, FlAsH-TMR, quantum dot-TMR and Cy3-Cy5.

8. The method of claim 1, wherein the intact cell is selected from the group consisting of mammalian cells, avian cells, insect cells, bacterial cells, yeast cells and plant cells.

9. The method of claim 1, wherein the first label and second label together form a pair, wherein each of the labels comprises at least one photo-active component, and wherein said pair is a donor-quencher pair or a fluorescent donor-acceptor pair.

10. The method of claim 1, wherein the detectable signal is radiation that emanates from energy transfer between the tRNA with a first label and at least one tRNA with a second label.

11. The method of claim 1, wherein the radiation is detected by anisotropy microscopy or by a fluorescence plate reader for a few seconds.

12. The method of claim 3, wherein the radiation is detected by anisotropy microscopy or by a fluorescence plate reader for a few seconds.

13. A method for measuring translation activity, which comprises:
  labeling at least one tRNA with a first label and at least one tRNA with a second label, wherein when the first label and the second label are in proximity a detectable electromagnetic radiation is produced;
  introducing into a biological sample the at least one tRNA labeled with the first label and the at least one tRNA labeled with the second label, wherein said labels produce electromagnetic radiation in response to overall protein translation activity in said biological sample, wherein said biological sample is an intact cell;
  detecting said electromagnetic radiation from the sample;
  analyzing said electromagnetic radiation produced in response to overall protein translation activity,
  wherein the analyzing comprises the step of computing the number of events (N) over a period of time t, wherein $$N \sim \frac{\sum I_t^2}{\sum \delta I_t^2}$$

wherein the step of analyzing produces a readout of a parameter of translation activity, wherein the parameter is rate of translational activity; and
  comparing said readout to a reference standard thereby determining an estimate of overall translation activity in real time without identifying a protein synthesized.

14. The method of claim 13, wherein the radiation is detected by anisotropy microscopy or by a fluorescence plate reader for a few seconds.

15. A method for measuring translation activity, which comprises:
  labeling at least one tRNA with a first label and at least one tRNA with a second label, wherein when the first label and the second label are in proximity a detectable electromagnetic radiation is produced;
  introducing into a biological sample the at least one tRNA labeled with the first label and the at least one tRNA labeled with the second label, wherein said labels produce electromagnetic radiation in response to overall protein translation activity in said biological sample, wherein said biological sample is an intact cell;
  detecting said electromagnetic radiation from the sample;
  analyzing said electromagnetic radiation produced in response to overall protein translation activity,
  wherein the step of analyzing produces a readout of a parameter of translation activity, wherein the parameter is rate of translational activity; thereby obtaining an estimate of overall translation activity; and
  comparing said readout to a reference standard thereby determining an estimate of overall translation activity in real time without identifying a protein synthesized.

* * * * *

UNITED STATES PATENT AND TRADEMARK OFFICE
CERTIFICATE OF CORRECTION

PATENT NO. : 9,012,171 B2
APPLICATION NO. : 12/682212
DATED : April 21, 2015
INVENTOR(S) : Smilansky It is certified that error appears in the above-identified patent and that said Letters Patent is hereby corrected as shown below:

In the Claims

Claim 13, Column 34:
Line 3, after "detecting said electromagnetic radiation from the sample;" insert -- and --.
Line 14, after the equation at lines 8-13 and before the subparagraph "wherein the step of analyzing produces a readout of a", insert the following subparagraph:

-- wherein $I_t$ is the average signal strength at time t and $\delta I_t$ is the average signal deviation at time t, and --.

Signed and Sealed this
Eighteenth Day of August, 2015

Michelle K. Lee
*Director of the United States Patent and Trademark Office*